United States Patent
Gutsol et al.

(10) Patent No.: US 8,521,274 B2
(45) Date of Patent: Aug. 27, 2013

(54) METHODS FOR NON-THERMAL APPLICATION OF GAS PLASMA TO LIVING TISSUE

(75) Inventors: Alexander F. Gutsol, San Ramon, CA (US); Alexander Fridman, Marlton, NJ (US); Gennady Friedman, Richboro, PA (US); Gregory Fridman, Philadelphia, PA (US); Manjula Balasubramanian, Gwynedd Valley, PA (US)

(73) Assignee: Drexel University, Philadelphia, PA (US)

( * ) Notice: Subject to any disclaimer, the term of this patent is extended or adjusted under 35 U.S.C. 154(b) by 822 days.

(21) Appl. No.: 11/911,479

(22) PCT Filed: Apr. 25, 2006

(86) PCT No.: PCT/US2006/015380
§ 371 (c)(1),
(2), (4) Date: Sep. 24, 2009

(87) PCT Pub. No.: WO2006/116252
PCT Pub. Date: Nov. 2, 2006

(65) Prior Publication Data
US 2010/0145253 A1    Jun. 10, 2010

Related U.S. Application Data

(60) Provisional application No. 60/674,507, filed on Apr. 25, 2005.

(51) Int. Cl.
*A61N 1/06*    (2006.01)
(52) U.S. Cl.
USPC ................................................ 607/2; 606/32

(58) Field of Classification Search
USPC ................................................ 607/2; 606/32
See application file for complete search history.

(56) References Cited

U.S. PATENT DOCUMENTS

| 3,838,242 A | 9/1974 | Goucher |
| 3,903,891 A | 9/1975 | Brayshaw |
| 5,683,366 A | 11/1997 | Eggers et al. |

(Continued)

FOREIGN PATENT DOCUMENTS

| WO | WO 2004/105810 A1 | 12/2004 |
| WO | WO 2006/116252 A2 | 11/2006 |
| WO | WO 2010/009103 A2 | 1/2010 |

OTHER PUBLICATIONS

Brown, I.G., et al., "Growth of large patterned arrays of neurons using plasma methods," Plasma Physics and Controlled Fusion, 2003, 45(5), 547-554.

(Continued)

*Primary Examiner* — Joseph Stoklosa
(74) *Attorney, Agent, or Firm* — Woodcock Washburn, LLP

(57) ABSTRACT

Method for the non-thermal treatment of human or animal tissue with high-voltage electrical discharge plasma is disclosed. The disclosed method employs current through plasma and through tissue not for the purpose of heating the tissue, but instead to maintain the plasma proximate to the tissue being treated. Also disclosed is a method of limiting the current through plasma and through tissue to minimize tissue heating by placement of an insulator or semiconductor between an electrode and tissue resulting in generation of a high-voltage discharge similar to a dielectric barrier discharge. The disclosed non-thermal plasma treatment can be employed to promote coagulation of blood, sterilization, disinfection, re-connection of tissue, and treatment of tissue disorders without causing significant thermal tissue damage.

19 Claims, 22 Drawing Sheets

(56) References Cited

U.S. PATENT DOCUMENTS

| | | | |
|---|---|---|---|
| 6,056,747 | A | 5/2000 | Saadat et al. |
| 6,099,523 | A | 8/2000 | Kim et al. |
| 6,213,999 | B1 | 4/2001 | Platt, Jr. et al. |
| 6,416,508 | B1 | 7/2002 | Eggers et al. |
| 6,482,201 | B1 | 11/2002 | Olsen et al. |
| 6,565,558 | B1 | 5/2003 | Lindenmeier et al. |
| 6,629,974 | B2 | 10/2003 | Penny |
| 6,723,091 | B2 | 4/2004 | Goble et al. |
| 2001/0020167 | A1 | 9/2001 | Woloszko et al. |
| 2001/0034519 | A1 | 10/2001 | Goble et al. |
| 2002/0026186 | A1 | 2/2002 | Woloszko et al. |
| 2004/0054366 | A1 | 3/2004 | Davison et al. |
| 2005/0118350 | A1 | 6/2005 | Koulik et al. |
| 2006/0009763 | A1 | 1/2006 | Goble et al. |
| 2006/0084158 | A1 | 4/2006 | Viol |
| 2006/0149129 | A1 | 7/2006 | Watts et al. |
| 2006/0293653 | A1 | 12/2006 | Van Wyk |
| 2007/0213700 | A1 | 9/2007 | Davison et al. |
| 2010/0010485 | A1 | 1/2010 | West, Jr. |
| 2011/0022043 | A1 | 1/2011 | Wandke et al. |

OTHER PUBLICATIONS

Chu, P.K., et al., "Plasma surface modification of biomaterials," Material Science and Engineering, 2002, R36, 143-206.

Fridman, G., et al., "Bio-medical applications of non-thermal atmospheric pressure plasma", Plasma Medicine Lab, Drexel Plasma Institute, Drexel University, Philadelphia, Pennsylvania, 2005, 5 pages.

Fridman, A., et al., "From plasma biology to plasma medicine: sterization, tissue engineering treatment of surface wounds and skin disease," The 58th Annual Gaseous Electronics Conference, Oct. 16-20, 2005.

Fridman, G., et al. "Use of non-thermal atmospheric pressure plasma discharge for coagulation and sterilization of surface wounds," ISPC-17, Toronto, Canada, Aug. 7-12, 2005, 1066-1067 and 665.

Ginsberg, G.G., "The argon plasma coagulator," Gastrointestinal Endoscopy, 2002, 55(7), 807-810.

Moisan, M., et al., "Plasma sterilization, methods mechanisms," Pure and Applied Chemistry, 2002, 74(3), 349-358.

Raiser, J., et al., "Argon plasma coagulation for open surgical and endoscopic applications:state of the art", *J. Phys.D: Appl. Phys.* 39, (2006), pp. 3520-3523.

Stoffels, E., "Biomedical applications of electric gas discharge," High Temperature Material Processes, 2002, 5(2), 191-202.

Vasilets, V.N., et al., "The study of the action of high frequency discharge plasma on polyethylene surface," High Energy Chemistry, 1978, 12(N5), 442-447.

PCT Application No. PCT/US2009/050509 : International Search report and Written Opinion of the International Searching Authority, Feb. 23, 2010, 13 pages.

PCT Application No. PCT/US2009/050509 : International Preliminary Report on Patentability, Jan. 18, 2011, 7 pages.

Kalghatgi et al., "Mechanism of Blood Coagulation by Nonthermal Atmospheric Pressure Dielectric Barrier Discharge Plasma", IEE Transactions on Plasma Science, Oct. 2007, 35(5), 1559-1566.

FIG. 8A   FIG. 8B

METHODS FOR NON-THERMAL APPLICATION OF GAS PLASMA TO LIVING TISSUE

CROSS REFERENCE TO RELATED APPLICATIONS

This application is a national stage entry of PCT Application PCT/US2006/015380, filed Apr. 25, 2006, and published as WO 2006/116252, which claims priority to U.S. Patent Application Ser. No. 60/674,507, filed Apr. 25, 2005, each of which is incorporated by reference herein in its entirety.

GOVERNMENT INTERESTS

This invention was made with government support under Contracts W81XWH-04-1-0419 and W81XWH-05-2-0068 awarded by the U.S. Army (MRMC). The government has certain rights in the invention.

BACKGROUND OF THE INVENTION

1. Field of the Invention

The invention relates to the field of non-thermal plasma. In particular the invention relates to methods and apparatus for application of non-thermal plasma.

2. Description of the Related Technology

Plasma is often described as the fourth state of matter. Typically it contains charged electrons and ions as well as chemically active species such as ozone, hydroxyl radicals, nitrous oxides, electronically excited atoms and molecules. Electronic excitation of some atoms and molecules in plasma produces ultraviolet radiation (hereinafter "UV"). Plasma can also be a good electrical conductor due to the presence of charged particles in the plasma. In a room-temperature environment, plasma is usually supported by electro-magnetic fields. Light electrons absorb energy from an electric field and transfer part of this energy to heavy particles in the plasma. Plasma is considered to be thermal if the rate of the electron energy transfer is fast relative to the rate of energy losses by heavy particles. In this case heavy particles reach energies comparable with the energy of electrons and the plasma becomes hot. In other cases, when electrons are not given sufficient opportunity to transfer their energy, heavier plasma components remain at much lower temperatures than the electrons. Such plasmas are called non-thermal and their gas temperatures can be as low as room temperature.

Plasma resulting from electric discharges has been employed in the past for cauterization which primarily involves transfer of thermal energy to tissue. An example of such treatment is a treatment which uses the Argon Plasma Coagulator™ (hereinafter "APC") and related types of equipment. These devices create plasma in a flowing gas (such as argon) using a radio frequency (hereinafter "RF") electromagnetic field. Plasma in these devices plays the role of a soft electrode which is used to transfer substantial current (usually greater than 150 milli-Amperes and possibly exceeding 1 Ampere for short periods of time) into the tissue. This results in rapid heating of the tissue to over 100° C., typically causing tissue desiccation and damage. FIGS. 1a-1c show examples of damage that may be caused by use of thermal plasma for tissue treatment. FIG. 1a shows tissue overheating caused by thermal plasma. FIG. 1b shows puncturing of the skin tissue as a result of contact with thermal plasma. FIG. 1c shows schar formation on the skin tissue that may be caused by thermal plasma. It should be mentioned that, in more conventional electro-cautery devices, conducting electrodes made of solid materials are employed to transfer currents that heat the tissue. Tissue can stick to the solid electrodes upon heating and the use of plasma in place of a solid electrode circumvents this problem in APC, for example.

Thermal plasma devices that do not rely on delivery of current into tissue have also been developed for coagulation and cauterization of tissue. Instead, the plasma is employed to rapidly heat a gas. The heated gas (often argon due to its inert properties) is subsequently directed toward the tissue in the form of a jet whereby the heated gas transfers its thermal energy to the tissue. Examples of devices for implementation of this type of technology are the PlasmaJet™ distributed by Plasma Surgical Limited and systems patented by Rhytech Corporation (U.S. Pat. Nos. 6,629,974 and 6,723,091, and U.S. Published patent application no. US2006/0009763). The effect of such plasma treatment is mostly thermal because many of the active chemical species in the remotely created plasma are short-lived and do not survive transport of the heated gas flow to the tissue.

Thus, it is well known than electrical discharge plasma has a very strong influence on living tissue. This strong influence can be of two kinds: thermal and non-thermal. Thermal influence of plasma which results in rapid heating of living tissue is well studied and is used for, for example, cauterization. In other cases the thermal influence of plasma results in living tissue desiccation and burns and thus is undesirable.

The non-thermal influence of electrical discharge plasma, caused by active plasma particles (electrons, ions, radicals, and other chemically active species) and UV radiation, may be useful in many cases, for example, for living tissue disinfection and sterilization, for skin disease treatment, for blood coagulation, etc. The closer to the living tissue the active plasma is located and the higher is electrical field in the plasma, the higher the intensity and efficacy of the non-thermal plasma treatment. Available methods of non-thermal plasma treatment are relatively weak and are effected usually by plasma jet or afterglow treatment because there are limitations on the power flux to the living tissue (to prevent overheating of the tissue) and on the total current and current density which may flow through the living tissue (to prevent damage of the tissue and nerve channels). Since the power of electrical discharge that creates plasma is a product of the discharge current and voltage, the higher the voltage—the lower the current, when power is fixed.

To increase efficacy of non-thermal plasma treatment and to overcome existing limitations, the present invention employs tissue as an electrode of a high-voltage electrical discharge with relatively low total current and current density. Under these conditions, the highest concentration of active plasma factors are located in close proximity to the treated living tissue, while the temperature of the plasma remains low because of the use of a relatively low total discharge power. In addition, total current and current density will also be low to ensure that tissue and nerve channels are not damaged.

Non-thermal plasmas have been developed. Non-thermal plasma discharges are used for the sterilization of equipment and various implantable plastics, for biochemical surface functionalization and treatment, and for many other applications. However, as far as the inventors are aware, non-thermal plasma technology has not been used for the various medical applications described herein, where plasma is in direct electrical contact with living tissue and acts on living tissue through various plasma-chemical processes, rather than primarily by transfer of thermal energy.

Therefore, there exists a need for providing a method for living tissue treatment by plasma without causing thermal damage.

SUMMARY OF THE INVENTION

In a first aspect, the present invention relates to a method of non-thermal treatment of living tissue by electrical discharge plasma wherein the plasma is maintained proximate to the living tissue by a current that passes through the plasma and the living tissue. The current passing through the tissue in the present invention is not used to heat the tissue, but rather is used to maintain the plasma proximate to the living tissue being treated. For this reason, the current employed in the present invention is kept below a value that would cause any significant tissue heating and resulting thermal damage.

In a second aspect, the present invention relates to a method of creating non-thermal plasma proximate to the living tissue being treated, wherein the current passing through the living tissue and the plasma is limited by the presence of an insulator or semiconductor between an electrode and the living tissue.

In a third aspect, the present invention relates to a method for treating a wound with a non-thermal plasma discharge including the steps of generating a non-thermal plasma discharge and contacting a wound with the generated non-thermal plasma.

In a forth aspect, the present invention relates to a method for enhancing coagulation of blood with a non-thermal plasma discharge including the steps of generating a non-thermal plasma discharge and contacting blood with the generated non-thermal plasma.

In a fifth aspect, the present invention relates to a method for disinfection and sterilization of living tissue with a non-thermal plasma discharge including the steps of generating a non-thermal plasma discharge and contacting an area to be sterilized with the non-thermal plasma.

In a sixth aspect, the present invention relates to a method for treatment of skin disorders with a non-thermal plasma discharge including the steps of generating a non-thermal plasma discharge and contacting an area of the skin exhibiting a skin disorder with the non-thermal plasma.

These and various other features of novelty that characterize the invention, and advantages of the invention are pointed out with particularity in the claims annexed hereto and forming a part thereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

FIGS. 8A-8E show Floating Electrode Dielectric Barrier Discharge (hereinafter "FE-DBD") treatment electrodes: FIG. 8A is a round electrode, FIG. 8B is a wand electrode, and FIG. 8C is a roller electrode, FIG. 8D is a micro-structured electrode and FIG. 8E is a mesh electrode.

DETAILED DESCRIPTION OF THE PREFERRED EMBODIMENT(S)

The present invention relates to apparatus and methods for employing a high-voltage plasma discharge for non-thermal tissue treatment to enhance blood coagulation, for sterilization, for bacteria and fungus inactivation, for treatment of ulcers and wounds, for treatment of tissue disorders and diseases, for tissue re-connection and sealing and for many other medical applications.

In a first aspect, the present invention relates to a method for non-thermal treatment of a human or animal body by high-voltage electrical discharge plasma which is generated proximate to the tissue being treated. Specifically, the plasma is sufficiently close to the tissue such that at least some of the plasma is maintained in immediate contact with tissue by passage of a small current through the tissue. The current is controlled so that it does not cause significant tissue heating, e.g. more than few degrees Centigrade.

There are many potential applications of electrical discharge plasma where the thermal effects of plasma on living tissue would be undesirable. Some of these applications include tissue disinfection and sterilization. Thermal damage to tissue during such a procedure would necessitate lengthy healing processes and use of anesthetics. Moreover, thermal damage to the surface of tissue might prevent sterilization of deeper tissue layers. Coagulation of blood without thermal tissue damage and desiccation would also help promote wound healing processes. In the absence of thermal damage, plasma could be used to promote natural processes in tissue through a combination plasma-chemical activity and LTV radiation. One application, for example, might be triggering of apoptosis in malignant tissue. Another might be tissue re-sealing or re-attachment after a surgical cut or injury. The last application might be particularly useful in liver resection surgery where it is difficult to re-attach parts of tissue after a cut. Tissue re-attachment might also be particularly useful when dealing with an injured spleen. Non-thermal plasma may also help seal connections between blood vessels against possible leaks during vascular surgeries. Non-thermal plasma helps establish mechanical connection between tissue parts through several possible mechanisms including plasma-chemical modification of bio-polymers on the surfaces of tissue and formation of fiber material during blood coagulation.

In a second aspect, the present invention relates to a method of generating such high-voltage electrical discharge plasma in contact with tissue by positioning an insulator or semiconductor between an electrode and tissue which limits the total current and current density through the plasma into the tissue. An apparatus for generating such a plasma discharge can be easily employed by a human operator, or by a remotely controlled machine, and is also suitable for telemedicine.

Figure 1A:
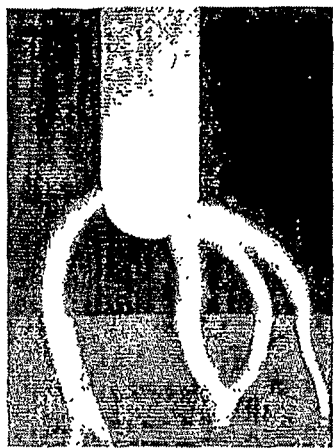
FIG. 1a shows tissue overheating caused by exposure to thermal plasma.
Figure 1B:
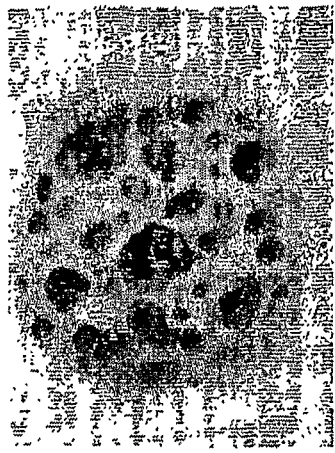
FIG. 1b shows puncturing of skin tissue due as a result of exposure to thermal plasma.
Figure 1C:
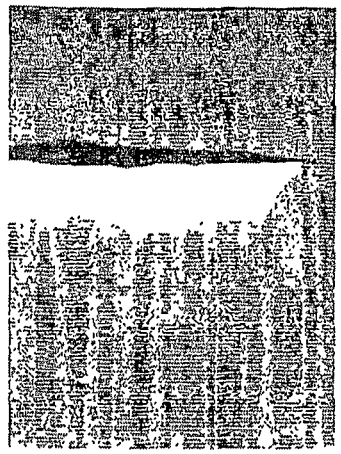
FIG. 1c shows char formation on the skin tissue caused by exposure to thermal plasma.
Figure 2:
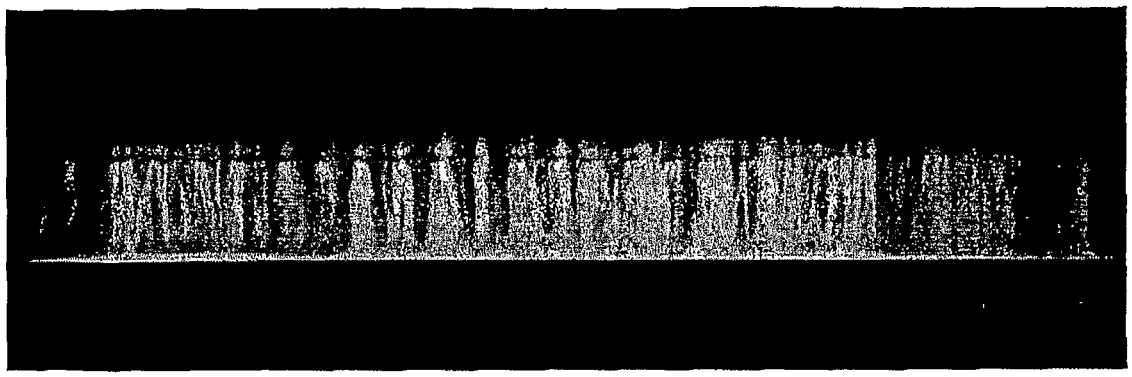
FIG. 2 shows a Dielectric Barrier Discharge (DBD) provided by a pair of electrodes and a dielectric barrier.

The high-voltage discharge generated as described in the foregoing paragraph, is similar to a Dielectric Barrier Discharge (hereinafter "DBD"), shown in FIG. 2, in that it may be created at standard atmospheric pressure and does not require or create high temperatures at the treatment location. For example, during DBD, the typical temperature rise is only a few degrees above room temperature.

The DBD is an alternating voltage discharge between two electrodes, at least one of which is typically covered by a dielectric. DBD plasma can be formed in the gas filled area, otherwise known as the discharge gap, between one electrode and a dielectric or between two dielectrics. The DBD is driven by an applied alternating high voltage (typically several kilovolts), which generates a high electric field between the electrodes. In the absence of a dielectric, the discharge starting from the first spark, would rapidly progress to a low-voltage arc discharge, as the electrons in the spark would initiate a series of ionization events, leading to very high current and ultimately to arc formation. The dielectric prevents arc formation by accumulating charge on the surface and generating an electric field that opposes the applied field, thereby limiting the current and preventing uncontrolled discharge development. Alternation of high voltage polarities ensures formation of this discharge in each half of the voltage cycle. Usually, DBD operates in the kilohertz range, so plasma between the electrodes does not have enough time to extinguish completely, and the discharge looks like a continuous glow and/or stationary or moving filaments in the discharge gap.

DBD is a typical discharge for non-thermal or cold plasma generation. In thermal plasmas, the temperatures of all plasma components (electrons, ions, gas molecules and atoms) are similar. Plasma can exist for some time if the plasma components are in dynamic equilibrium: recombination of electrons and ions should be balanced by ionization. To provide significant ionization, it is necessary to have energetic particles, usually electrons, with energies of several electron-volts (eV). The average energy of gas particles equals about 1 eV and corresponds to the gas temperature of 11,600 K. This means that more or less stable thermal plasmas always have temperatures above 5000 K.

In non-thermal plasmas, temperatures of components can be very different and do not have to be in equilibrium. Usually the temperature of electrons is much higher (more than 10,000 K) than the temperature of heavy particles, such as ions and gas molecules. Typically, low-temperature plasma exists in luminescent lamps. Gas temperatures of the non-equilibrium plasma can be very different and may range from room or ambient temperature to several thousand degrees Kelvin. Plasma is considered to be non-thermal when its gas temperature is not considerably higher than the surrounding temperature, which surrounding temperature may be, for example, room temperature (e.g. 20-25° C.). For the purposes of this invention, non-thermal plasma can be characterized by an average plasma gas temperature that does not exceed 100° C. The plasma electron and ion density may be about $10^{11}$ $cm^{-3}$ to about $10^{13}$ $cm^{-3}$, and, more preferably, above $10^{12}$ $cm^{-3}$. Electron density in DBD filaments, for example, may be about $10^{13}$ $cm^{-3}$ and electron temperatures can range from 10,000 to 30,000 K.

It is important to stress that the temperature rise in tissue obtained by transferring heat from the surrounding matter depends not only on the temperature of the surrounding matter, but also on its volume, on the tissue volume, on the heat capacities of the tissue and the surrounding matter, on the ability of the surrounding matter and tissue to conduct heat, and on the time of contact. For this reason, when non-thermal plasma is employed, the treatment process can be controlled so that tissue temperature does not rise above 50° C.

In one apparatus according to the invention, the non-thermal plasma discharge may be generated by a high frequency oscillation of high voltage of from about 5 to about 20,000 kHz, optionally, from about 10 to about 30 kHz, using a voltage of about 2 to about 50 kV, optionally, from about 10 to about 30 kV. Whereas the DBD, shown in FIG. 2, is created by applying a high frequency voltage between two electrodes, the non-thermal plasma discharge used in this invention occurs in a highly localized region between an insulated electrode and a second electrode. The second electrode may be a nearby object, and, in many applications of the present invention the second electrode is a human or animal body.

It is typically not necessary that the human or animal body be grounded or connected to a second electrode since the plasma discharge is controlled such that the human or animal body is typically large enough, relative to the size of the plasma discharge, to allow the charge to dissipate. However, as a precaution, or if it is desirable to employ a relatively high charge, a second electrode, ground or both, may be included in the apparatus. It is also possible to have a body connected to a second electrode connected to a power supply, or alternatively to have the body grounded to the power supply via a grounding component in order to have a closed loop, if desired.

Figure 3:
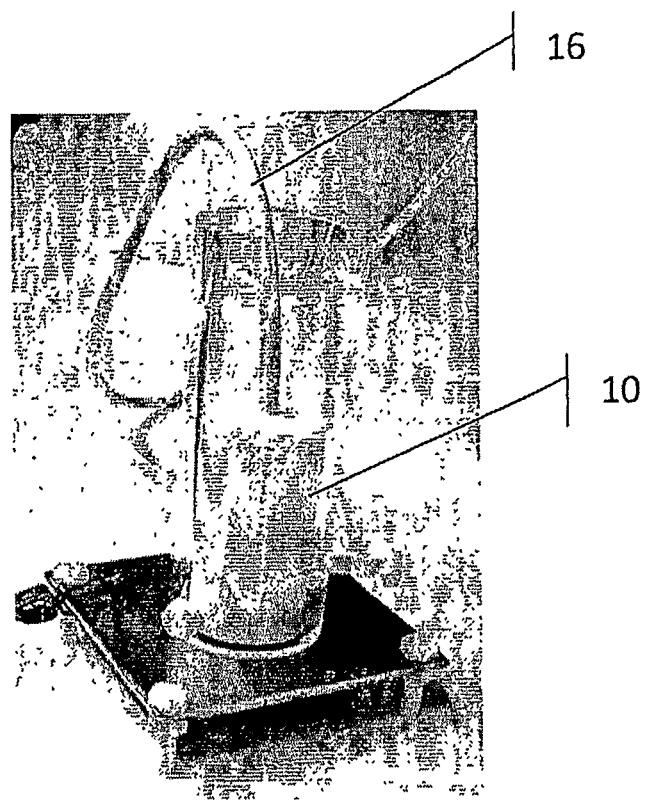
FIG. 3 shows an energized electrode which may be used in the non-thermal plasma treatment method.

In one embodiment of an apparatus of the present invention, a substantially completely insulated electrode 10, shown in FIG. 3, is energized by a high frequency, high voltage power source. No voltage is applied to the nearby object. In this embodiment, the object which may be a human or animal body, acts as a floating electrode. For this reason this nonthermal plasma discharge may be referred to as a floating electrode dielectric barrier discharge (FE-DBD).

The geometry of the non-thermal plasma discharge is controlled by the shape and size of energized electrode 10. The ability to perform treatment without directly applying a voltage to the human or animal body, and the ability to limit the discharge current to, for example, less than about 50 milli-amperes, and, optionally, to less than 1 milli-ampere, reduces the risk of harm to the surrounding tissue or the nerve system. The non-thermal plasma discharge is a high-voltage discharge. The value of the electric field near the surface of the living tissue may exceed 200 V/mm in the moments of maximal current, and, optionally, the value of the electric field near the surface of the living tissue may exceed 500 V/mm in the moments of maximal current.

Figure 5:
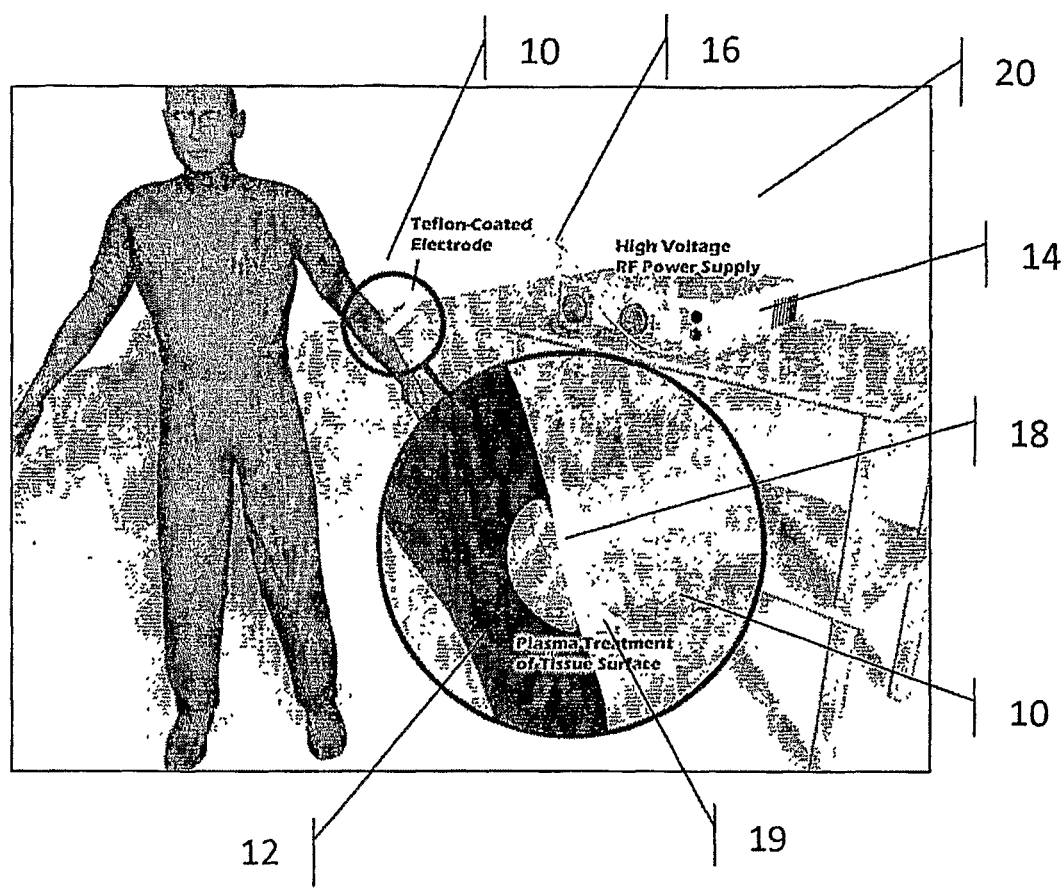
FIG. 5 shows a diagram of a non-thermal plasma device as used in the treatment of a patient.

The application of an exemplary plasma device 20 is shown in FIG. 5. Electrode 10 delivers between 0.01 W/cm$^2$ and 50 W/cm$^2$, and optionally between 0.1 W/cm$^2$ and 2 W/cm$^2$ of plasma power, averaged over one square millimeter of the treatment area, and has a Teflon® coating. Electrode 10 is connected to power supply 14, which is a high voltage RF power supply, via cord 16. Power supply 14 may be made portable by reducing its size, power consumption, and enabling it to be battery operated. Electrode 10 is then placed proximate to treatment area 12 and activated. Power supply 14 and electrode 10 may be within the same housing in order to minimize the size of device 20 and to enable it to be portable. The human or animal body acts as a floating potential electrode if the plasma gap 19 between electrode 10 and treatment area 12 is maintained at or below a suitable distance. A skilled person is able to routinely determine a suitable plasma gap 19 for a particular non-thermal plasma discharge.

Figure 7:
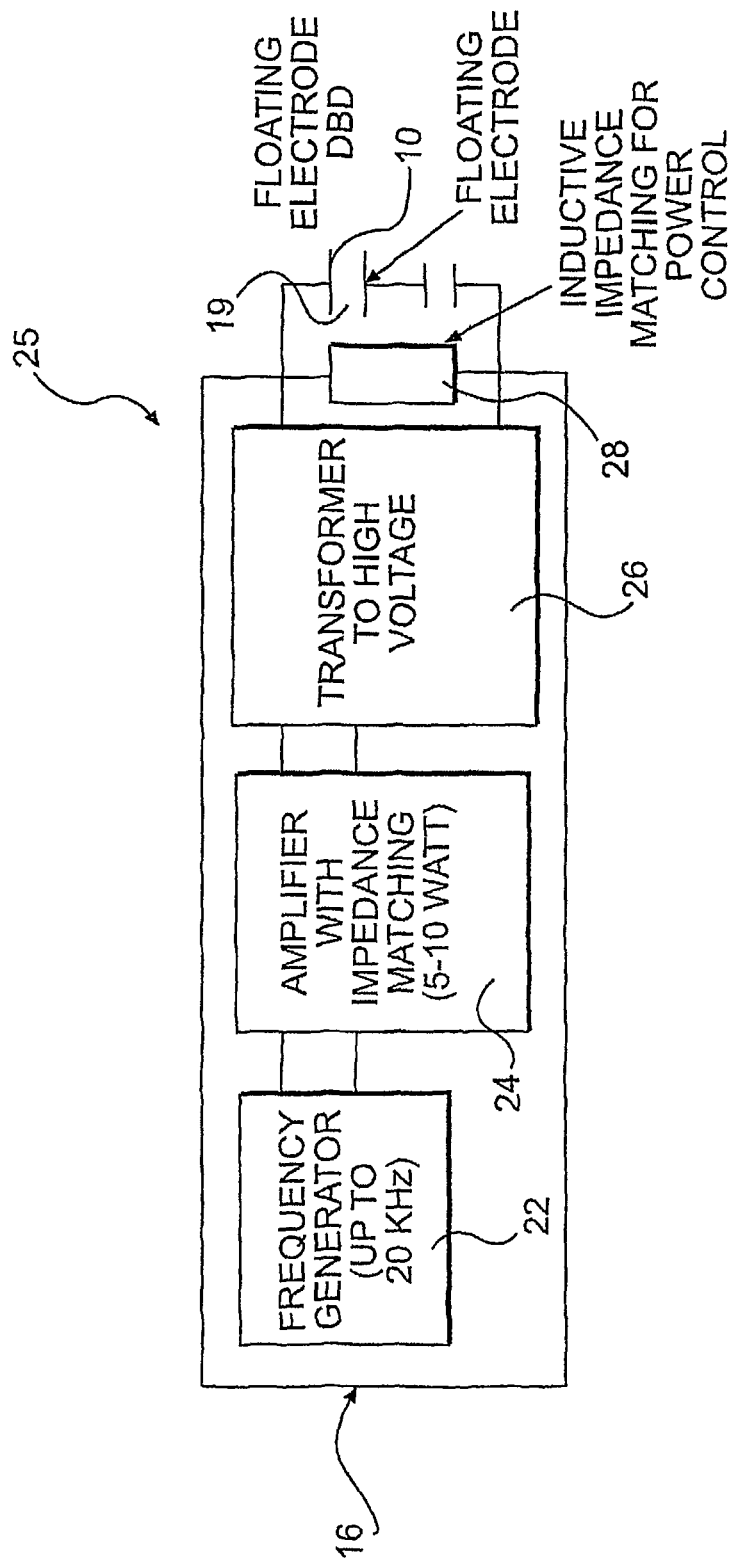
FIG. 7 shows an electrical diagram of a non-thermal plasma and a power supply.

FIG. 7 shows an electric diagram of an apparatus which employs a human or animal body acts as a floating electrode. Plasma device 25 of FIG. 7, includes apparatus for control of the size of plasma gap 19, as well as use of different sizes and shapes of electrodes. The plasma gap is typically from about 0.5-5 mm. The electrodes for treatment of the human or animal body typically have surface areas of about 0.1-10 cm$^2$. The variations in electrode size and shape permit finer control of the size and shape of the treatment area, allowing the operator to customize the treatment. This is advantageous since it avoids unnecessary plasma treatment of healthy tissue surrounding the treatment area.

Figure 8C:
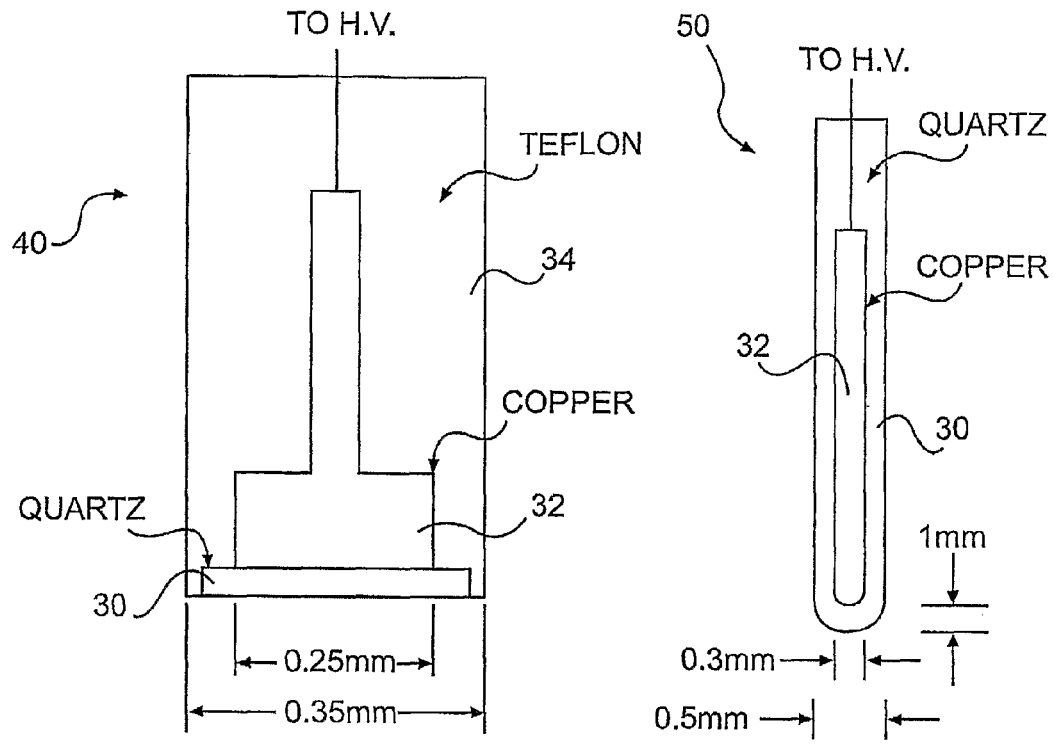
Figure 8C:
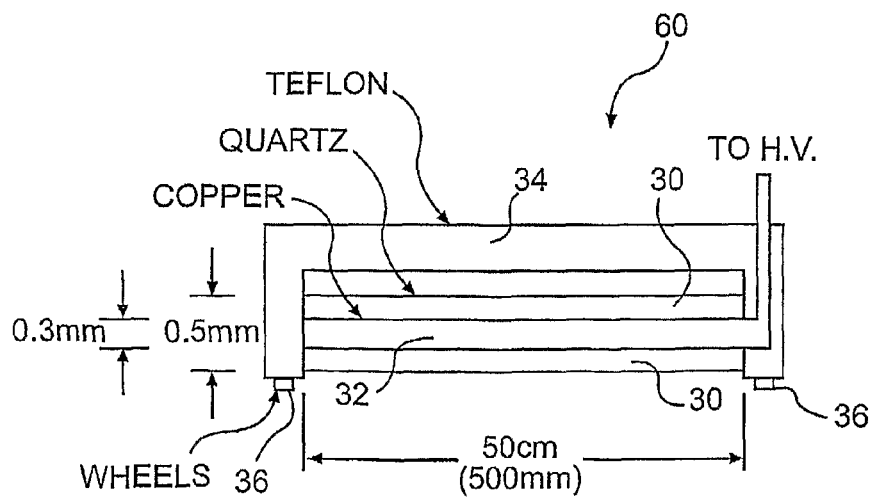

FIGS. 8A-8E show five different embodiments of different types of electrodes that may be used do deliver a non-thermal plasma discharge in accordance with the present invention. FIG. 8A is a round electrode 40 formed from an insulator 30, a conductor 32 and a coating 34. Coating 34 may also function as an insulator. FIG. 8B is a wand electrode 50 formed from an insulator 30 and a conductor 32. FIG. 8C is a roller electrode 60 formed from insulators 30, conductor 32 and coating 34. The roller electrode 60 includes wheels 36 to facilitate its use.

Figure 8D:
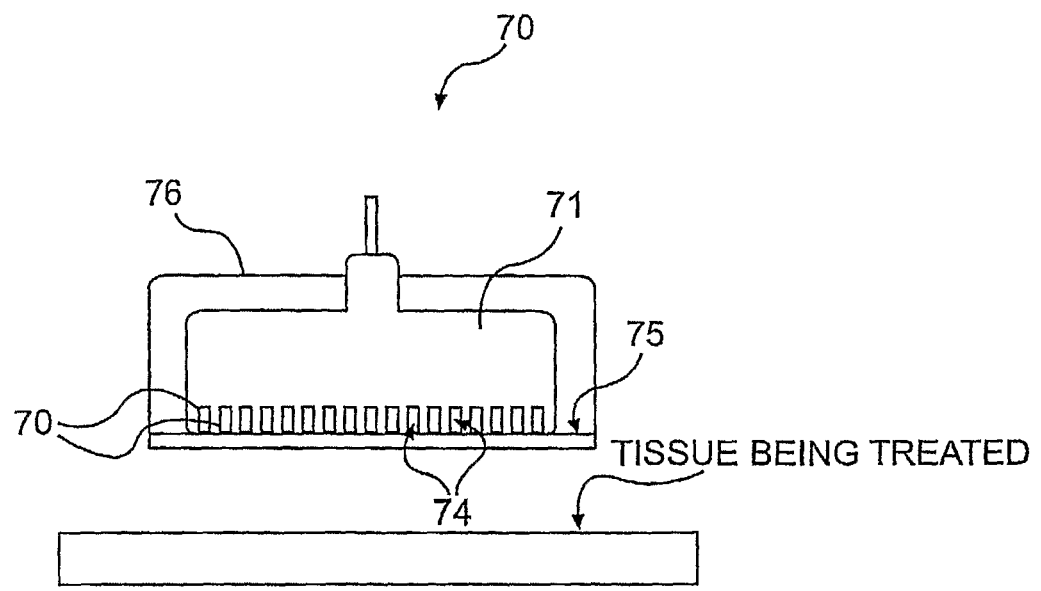

FIG. 8D is a micro-structured electrode 70. Micro-structured electrode 70 may include a conductor 71 having gaps or voids 72 which are filled with an insulator or dielectric material 74. Other insulators or dielectrics 75, 76 are provided and may be made from the same or different materials. Micro-structured electrode 70 is also provided with a high voltage connection 78 for connection to a power source, not shown. This type of micro-structured electrode 70 can be employed to customize the properties of the electric plasma discharge for specific purposes. The gaps or voids 72 can be employed to alter the properties of the plasma discharge.

Figure 8E:
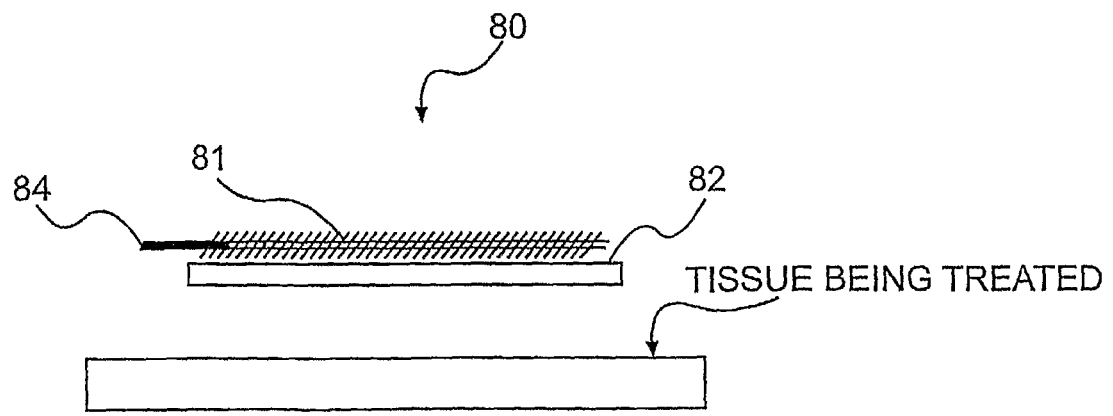

FIG. 8E is a mesh electrode 80. Mesh electrode 80 includes a conductor 81 in the form of a conductive mesh, preferably made from metal or another suitable conductive material. The conductor 81 is covered with an insulator or dielectric 82 and is provided with a high voltage connection 84 for connection to a power source, not shown. Mesh electrode 80 can be employed to provide customizable properties of the electric discharge plasma and may also be used to facilitate viewing of the treatment area by providing a transparent insulator or dielectric 82 which allows viewing of the treatment area through the conductive mesh and transparent insulator.

Exemplary materials for each of the insulator, conductor and coating are indicated in the figures. However, other suitable materials may be employed for each of the insulator, conductor and coating and selection of materials is within the ability of the skilled person. For example, the electrode may be a highly polarizable fluid in certain embodiments of the invention. This fluid may be contained within a solid enclosure, within plastic tubing or other fluid container. The use of a transparent fluid as an electrode may provide better visual access to the treatment area, for example. The electrode may also be segmented into a mesh-like structure, if desired. Using a segmented electrode may not only improve visual access to the treatment area, but may permit better control over the micro-structure of the plasma discharge, including smaller or greater density of the discharge filaments and overall discharge uniformity.

Figure 9:
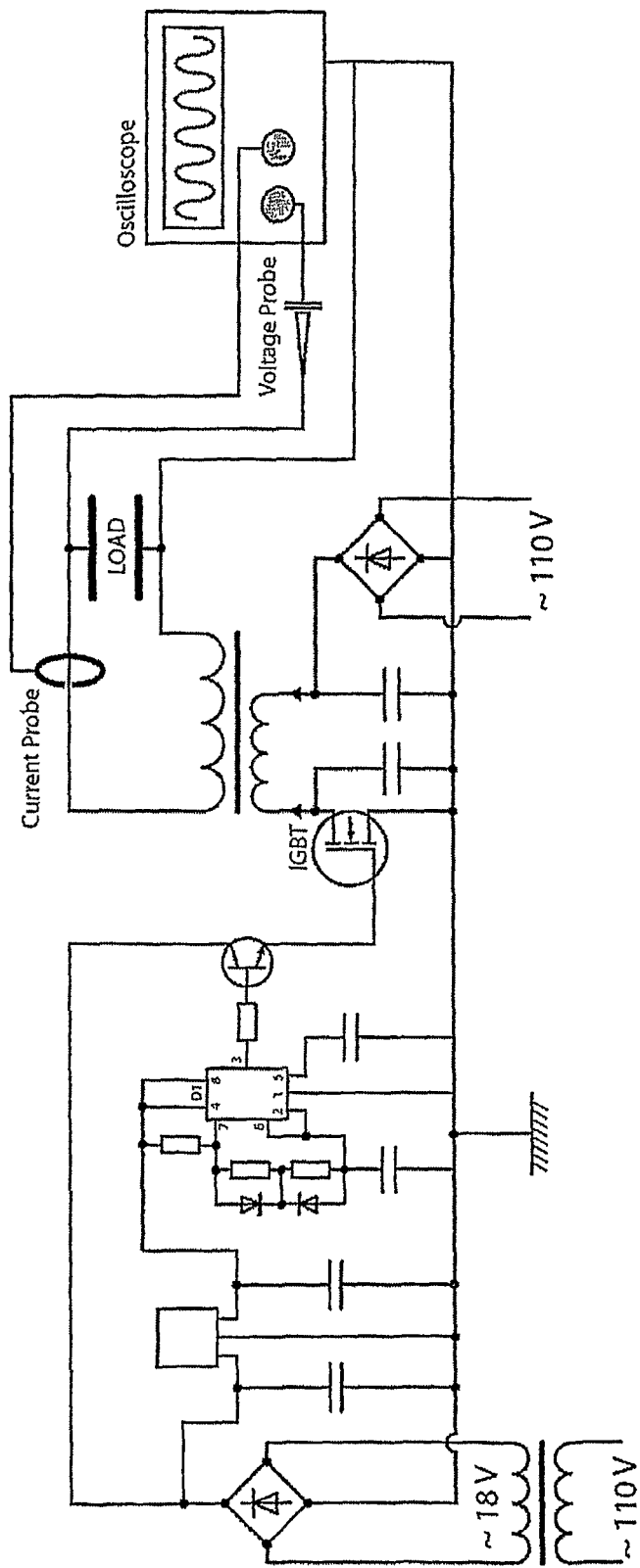
FIG. 9 shows FE-DBD power supply schematic and power analysis setup schematic.
Figure 10:
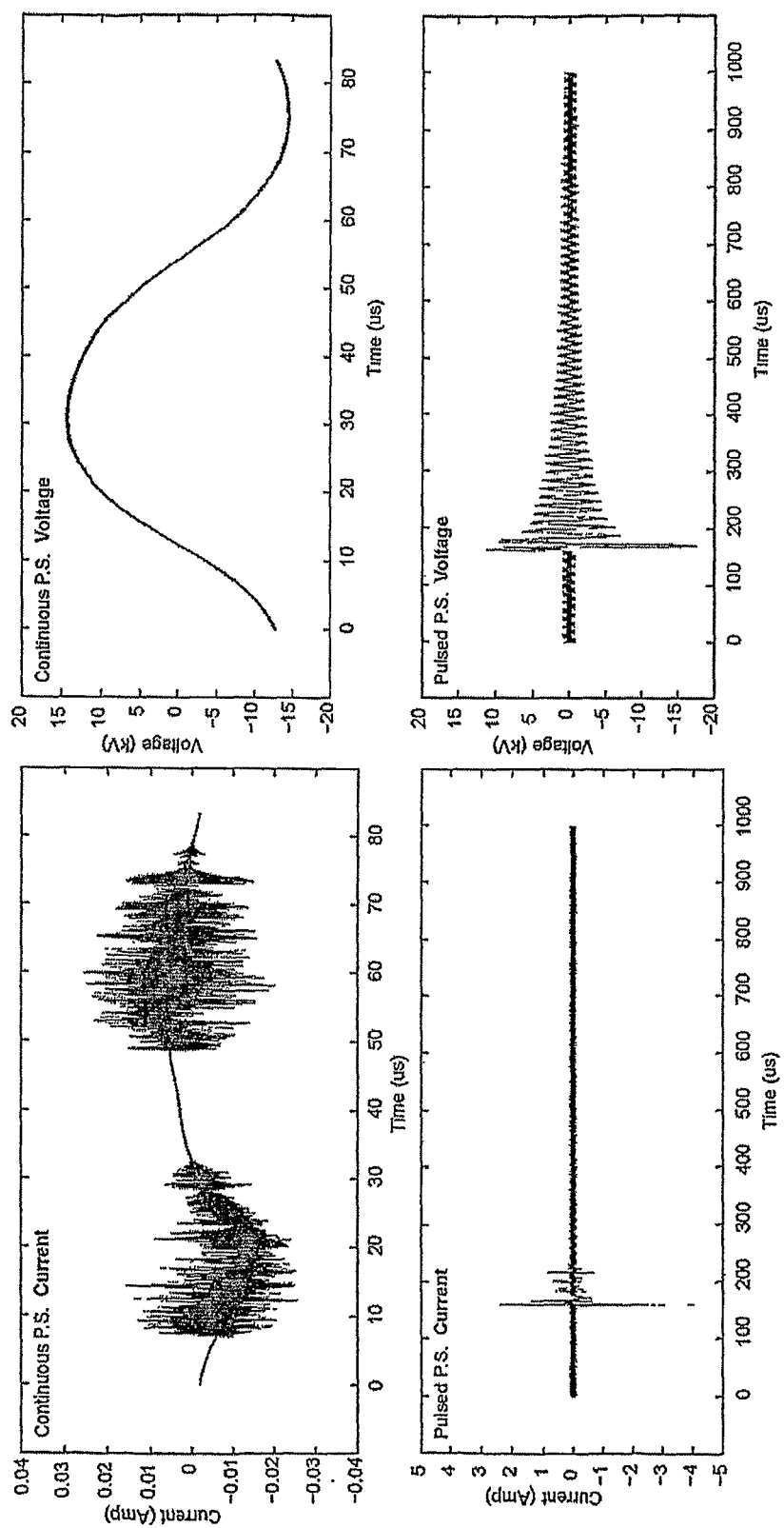
FIG. 10 shows the characteristic current and voltage signals per period for continuous wave and pulsed power supplies.

FIG. 9 shows a schematic of a suitable power supply and power analysis setup for implementation of the plasma discharge device of the present invention. Power analysis can be employed for monitoring variations in the applied power to customize the properties of the plasma discharge. FIG. 10 shows some characteristic current and voltage signals per period for continuous wave and pulsed power supplies that may be employed to generate a non-thermal plasma discharge in accordance with the present invention.

Plasma device 25 also includes a power supply 15 that permits control of necessary parameters of the discharge such as the applied power. Optionally, power supply 15 is also used to control of the frequency, the applied voltage, the current and to provide impedance matching. Power supply 15, shown in FIG. 7, also includes a frequency generator 22 that permits the use of frequencies of up to 20 KHz. Power supply 15 may also include an amplifier 24 to provide, for example, impedance matching of 5-10 watts. Also included are a transformer 26 and apparatus for inductive impedance matching 28 for power control. Power supply 15 for plasma device 25 offers the ability to fine tune the power used in providing the non-thermal plasma to enable fine control of the plasma application. Power supply 15 can be integrated as a single unit. It should provide generation of AC high voltage with necessary power.

This FE-DBD treatment has many applications in the medical field. This treatment can be useful for treating wounds, as well as for enhancing blood coagulation. Additionally, due to the potential for sterilization, plasma device 20 can also assist in preventing infections.

Furthermore, the apparatus of the present invention can be a highly portable device. This is especially helpful for those who have difficulty accessing health care. In addition, the plasma device of the present invention can be employed by emergency personnel so that treatment of injuries and disorders can begin immediately. Furthermore, there are many applications particularly relevant to the military where the non-thermal plasma device can be portable, remotely controllable, and possibly delivered by a machine. The device could also be used for treating post-operative infections, sterilization, bacteria inactivation and treatment of skin disorders.

In a first aspect of the method of the present invention, the invention relates to a method for the non-thermal treatment of a human or animal body with a high-voltage plasma discharge. This method involves the generation of a high-voltage plasma discharge between a first, insulated electrode and a human or animal body in a manner whereby the high-voltage plasma discharge contacts a treatment area.

Typically, the treatment area will include a wound of some kind. For purposes of this disclosure a "wound" is any cut, abrasion, or break in the skin or an organ, as well as various skin diseases and other disorders that affect skin and organ tissue.

In the method a wound may be exposed to a high-voltage plasma discharge. The high-voltage plasma discharge is used to coagulate blood, promote healing and/or sterilize the wound without causing unacceptable thermal damage to the surrounding tissue. Results on human blood and cadaver tissue confirm that the high-voltage plasma discharge promotes blood coagulation and sterilizes the wound without causing unacceptable damage to surrounding tissue.

The non-thermal plasma treatment may be carried out for any suitable length of time to promote wound healing, enhance blood coagulation or sterilize the wound, without causing unacceptable tissue damage. A suitable length of treatment time may be from about 5 seconds to about 5 minutes, and, optionally, from about 15 seconds to about 1 minute. The treatment time may vary depending on the properties of the specific plasma discharge employed, the nature of the wound and the apparatus employed to apply the discharge. Such variations are within the ability of skilled persons.

Blood coagulation and sterilization are believed to be stimulated by the large concentration of chemically active species in plasma such as ions, radicals, such as oxy-, hydroxyl-, and nitrogen radicals, electronically excited atoms and molecules, and ultra-violet (UV) photons. This treatment promotes healing of wounds, with the potential to expedite wound healing, enhance blood coagulation and reduce the incidence of infection. Without being bound by theory, it is considered that the present non-thermal plasma treatment catalyzes or enhances natural processes for blood coagulation.

Open wounds can be treated by non-thermal plasma in standard environmental conditions, i.e. at standard atmospheric pressure using air as the gas, or with addition of special gases as additives. Special gases can include pure gases, such as inert gases (argon, helium, etc.), organic substances (methane, ethane, other saturated and unsaturated hydrocarbon gases, hydroxy-carbonic compounds, etc.), oxygen, nitrogen, etc., and also special mixtures of, for example, an inert gas with alcohol vapor, etc.

Figure 4:
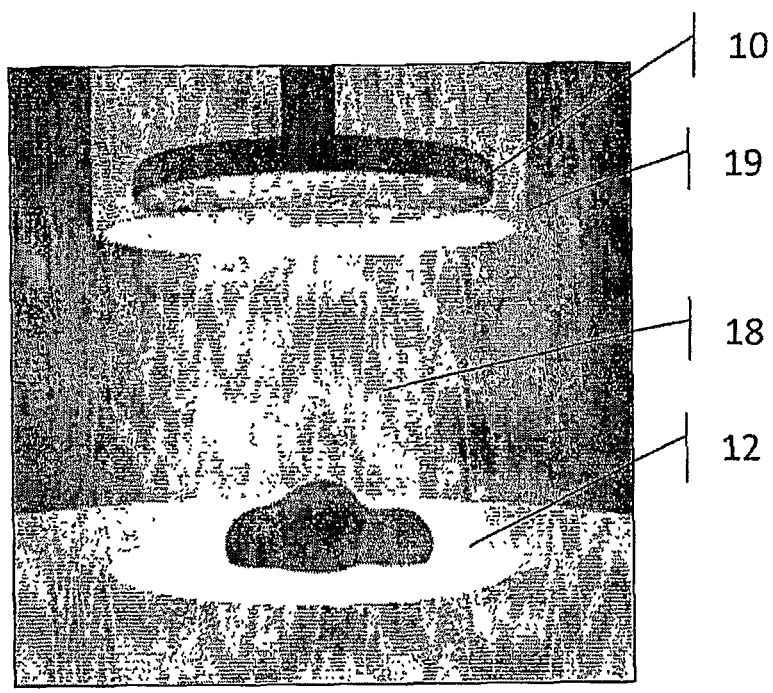
FIG. 4 shows a diagram of an electrode and a wound treatment area.

In the treatment, electrode 10 is positioned at a suitable distance from the wound to provide a plasma gap 19, shown in FIG. 4, located between electrode 10 and treatment area 12. The high-voltage plasma discharge 18 is created in plasma gap 19. Electrode 10, shown in FIGS. 3-5 can be covered by any suitable, conventional insulator such as quartz or polytetrafluoroethylene, more commonly known by its trade name Teflon®. In certain embodiments the insulator or semiconductor covers only a portion of the electrode surface. The insulator or semiconductor may be formed as a solid material in the form of a layer or a coating. In some embodiments, the insulator or semiconductor completely insulates the electrode from the tissue. This further increases the safety to patients because no exposed electrodes are used thereby preventing direct application of high voltage to the patient by inadvertent contact with the electrode 10, for example. In the treatment, gas in the gas discharge plasma may be caused to flow relative to the treatment area.

In addition, the high frequency power may be maintained below about 50 W/cm$^2$, and is optionally below about 2 W/cm$^2$ to reduce the potential for injury to the patient. Electrode 10 may be hand-held, or alternatively manipulated by a machine.

In another embodiment, the present invention may be employed for sterilization. In this embodiment, the high-voltage discharge may be applied to any surface or product to cause sterilization of the surface. Application of the high-voltage plasma discharge can be accomplished with a device containing a single insulated electrode, in cases where sterilization is carried out on a material suitable to function as a second, floating electrode, similar to the role of the human or animal body, as described above. Alternatively, a device including two insulated electrodes may be employed to generate non-thermal plasma in a gap between the electrodes and the non-thermal plasma can be applied for sterilization of a surface or product. The same parameters for plasma generation and treatment time, as described above, may be employed in this application of the present invention.

In a still further embodiment of the present invention, a non-thermal plasma discharge may be employed to inactivate bacteria, viruses, micro-organisms, or destroying certain proteins that may exist on or within the said tissue. In this method, bacteria, viruses, micro-organisms, or destroying certain proteins that may exist on or within the said tissue, can be selectively inactivated without any visible or microscopic tissue damage in humans or animals. Alternatively, the non-thermal plasma discharge may be employed for the purpose of destroying certain cells in the tissue, particularly cells located in a surface layer of the tissue. Destruction of cells by plasma-chemical processes, rather than by thermal damage, is the effect being sought in such applications because thermal damage is often much deeper and non-selective between different cell types. The plasma-chemical cellular destruction pathway likely offers greater selectivity between different cell types because of differences in cellular sizes, cellular membranes (permeability, chemical composition, thickness, etc.), and internal cellular processes (metabolism, replication, etc.). Again, the same parameters for plasma generation and treatment time, as described above, may be employed in this application of the present invention.

In yet another embodiment of the present invention, the high-voltage plasma discharge may be employed to treat skin disorders. Exemplary skin disorders which may be treated in this method of the present invention include abnormal cells such as melanoma or other skin cancer cells. It is thought that the application of a high-voltage plasma discharge induces apoptic-like behavior in abnormal cells.

Also, the high-voltage plasma discharge may be employed for non-thermal treatment of some diseases such as pathogen-induced skin diseases, with minimal or no damage to the surrounding tissue. For example, non-thermal plasma can be employed to selectively inactivate prokaryotic cells which may be involved in some pathogen-induced skin diseases. One example of such a skin disease is *Leishmania*, which is treated below in one of the examples.

The high-voltage plasma discharge of the present invention may also be employed for obtaining a cosmetic improvement of tissue. One example of such improvement may be elimination of acne. In many cases acne is caused by the presence of micro-organisms within pores of the skin and non-thermal plasma treatment can destroy such micro-organisms through various plasma-chemical means.

In addition, the high-voltage plasma discharge of the present invention may be employed for improving a mechanical connection between different parts of the tissue. This might be particularly useful in liver resection surgery where it is difficult to re-attach parts of tissue after a cut. Tissue re-attachment might also be particularly useful when dealing with an injured spleen. Non-thermal plasma may also help seal connections between blood vessels against possible leaks during vascular surgeries. Non-thermal plasma helps establish mechanical connection between tissue parts through several possible mechanisms including plasma-chemical modification of bio-polymers on the surfaces of tissue and formation of fiber material during blood coagulation. The same method of applying the plasma, as discussed above, is employed to accomplish these purposes.

EXAMPLES

Example 1

Figure 6A:
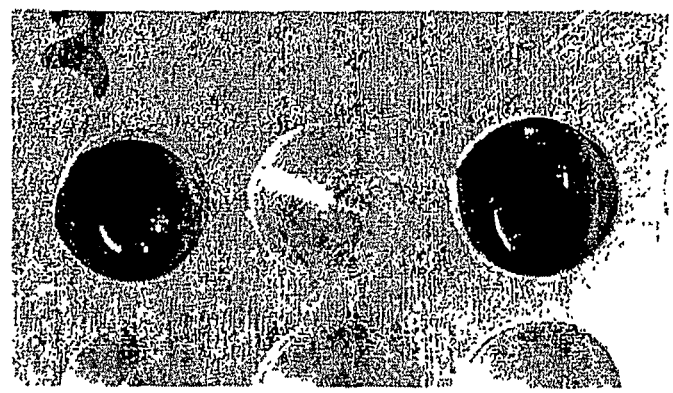
FIG. 6a shows a control blood sample and a blood sample that had been treated with non-thermal plasma for 15 seconds.
Figure 6B:
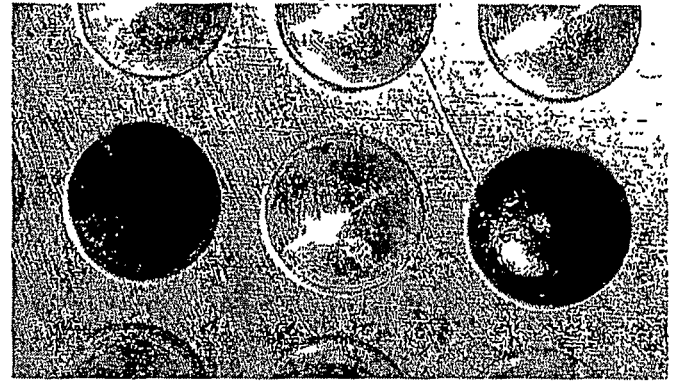
FIG. 6b shows a control blood sample and a blood sample that had been treated with non-thermal plasma for 1 minute.

Using plasma device 20, blood coagulation tests have been performed on blood from cadaver organs. The tests showed faster coagulation of the blood when exposed to the non-thermal plasma, as compared to coagulation without additional treatment. In one test, blood substantially coagulated within 15 seconds using the non-thermal plasma treatment, while the control sample took over 10 minutes to coagulate without the treatment. FIGS. 6a and 6b show blood samples that were used in testing. FIG. 6a shows the control sample on the left and the non-thermal plasma treated sample on the right. The sample on the right showed significant coagulation after 15 seconds of non-thermal plasma treatment.

FIG. 6b shows the same samples after 1 minute, with the sample on the right having been treatment for 1 minute with non-thermal plasma. It can be seen in FIG. 6b that the non-thermal plasma treated sample is markedly more coagulated than the control sample.

Example 2

Additional tests were performed on cadaver organs with subsequent gross and microscopic evaluation of tissue to assess tissue damage. The results demonstrated blood coagulation within 15 seconds without gross or microscopic evidence of tissue damage.

Example 3

Skin sterilization tests were also performed on cadaver skin. After non-thermal plasma treatment, cultures were taken from the skin. Assessment of these cultures demonstrated complete sterilization after a 6 seconds of treatment by the non-thermal plasma. The skin was further examined grossly and microscopically for damage. No significant tissue damage was found after as long as 5 minutes of non-thermal plasma treatment.

Examples 4-5

Blood Coagulation and Tissue Sterilization

Experimental Setup

A varying frequency and voltage power supply for generation of Floating Electrode Dielectric Barrier Discharge (hereinafter "FE-DBD") electric plasma (e-plasma) was based on a system consisting of a wave-form generator, amplifier, and a transformer. A wave-form generator (CFG253/280, Tektronix, Inc.; Richardson, Tex.) was used for generation of 0-22.5V rms sine, square, and triangular waves. The signal was then amplified (PowerTron 250A amplifier, 0-22.5V rms, Industrial Test Equipment Co. Inc., Port Washington, N.Y.) and stepped up to high voltage (Transformer, 22.5V rms primary and 20 kV secondary, Industrial Test Equipment Co. Inc., Port Washington, N.Y.) to achieve a desirable high voltage signal. Electric discharge generated by this power supply is sufficiently uniform for treatment of tissue and blood, where micro-patterns created by this and similar discharges are of no great importance.

E-plasma was generated between the insulated High Voltage Electrode and the sample (Floating Electrode) undergoing treatment. 1 mm thick polished clear fused quartz (Technical Glass Products, Painesville, Ohio), was used as an insulating dielectric barrier. Three electrodes were constructed for treatment of various shapes and configurations of samples (See FIG. 8). A round electrode (25.4 mm diameter) was used for treatment of samples where precise control of distance from the electrode to the sample was desired for increased repeatability of experimental results. Roller and wand electrodes were used as hand-held electrodes for treatment of varying shapes of samples where portability or large electrode area was more desirable than the precision of the treatment.

For power analysis of FE-DBD e-plasma in continuous or pulsed mode (FIG. 9—principal schematic, and FIG. 10—signal output), current passing through e-plasma and the voltage drop in the gap were measured. For current analysis we utilized a magnetic core current probe (1 Volt/Ampere +1/−0% Sensitivity, 10 nanoseconds usable rise time, 35 MHz bandwidth, Model 4100 Pearson Current Monitor, Pearson Electronics, Palo Alto, Calif.). Voltage was measured using a wide bandwidth voltage probe (PVM-4 1000:1, North Start High Voltage, Marana, Ariz.). Signals were acquired and recorded by a Digital Phosphor Oscilloscope (500 MHz bandwidth, $5 \cdot 10^9$ samples/s, TDS5052B, Tektronix, Inc, Richardson, Tex.) (FIG. 4). Acquired data was then integrated using MATLAB code (MATLAB Release 14, Mathworks, Inc. Natick, Mass.).

For all tests a round electrode fixed by micro-positioners at 2.7 mm from the treated sample for blood samples and 1.5 mm for tissue and agar samples was utilized. Distances of 2.7 and 1.5 mm were chosen based on maximum power input into plasma—capacitive power match to the transformer is best at 2.7 mm for liquid samples and 1.5 mm for tissue and agar samples.

Figure 11:
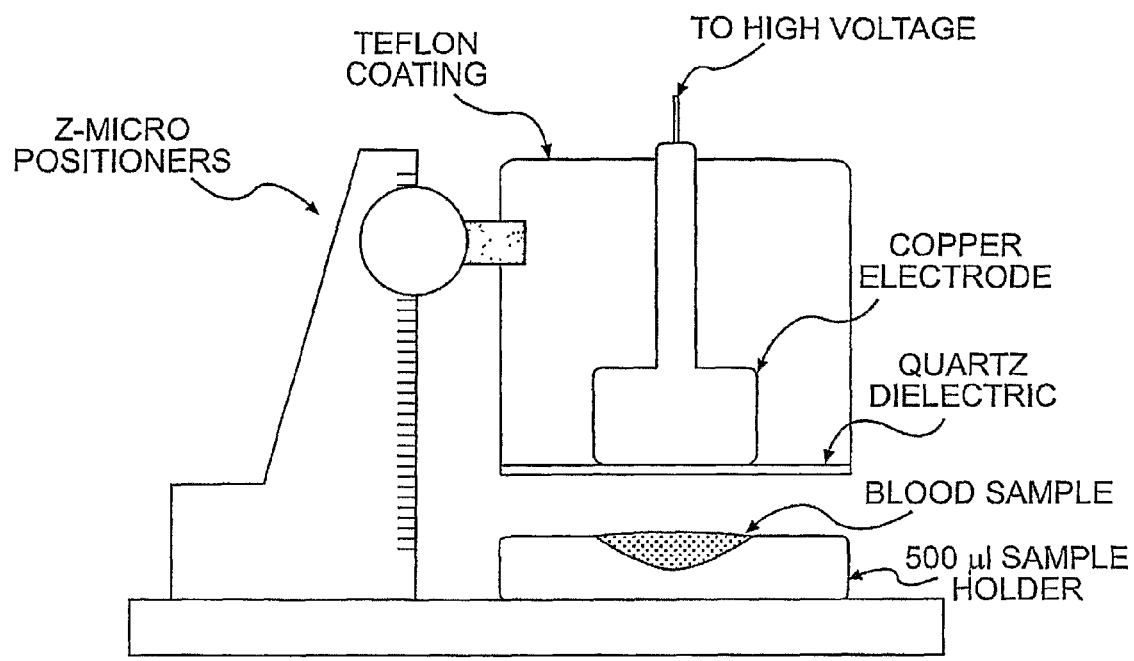
FIG. 11 shows an experimental setup for FE-DBD treatment of blood plasma samples.

For treatment of 500 µl blood samples a special setup was constructed. This setup allows for precise control over the distance from the top of the treated sample to the dielectric barrier. A volume of 500 µl was chosen as it is the minimum volume for testing. To achieve precise volume, a hole of 3.7 mm deep was cut by a 25.4 mm ball mill and then polished to eliminate any sharp edges. For e-plasma treatment of different volumes of blood plasma a set of four electrodes of different volumes were constructed: 0.5, 1, 1.5, and 2 ml. 19.1 mm tall acrylic was used as a base and stainless steel rods were inserted into a 12.7 mm through-hole. For 0.5, 1, 1.5, and 2 ml volumes 15.8 mm, 11.9 mm, 7.9 mm, and 4.1 mm tall stainless steel rods were used. Treatment of tissue samples was accomplished either by fixing a sample of skin on a stainless steel vacuum plate or by holding the electrode by hand over an organ (for hand-held treatment, the electrode was enclosed by a "jacket" to allow for precise distance control). During treatment of agar plates the electrode and the plate were held in place by micro-positioners (FIG. 11).

Example 4

Blood Coagulation

Blood plasma samples were analyzed utilizing the STA Compact® (Diagnostica Stago, Parsippany, N.J.) Prothrombin Time (PT), activated Partial Thromboplastin Time (aPTT), and Thrombin Time (TT) analyzer. Samples were obtained from healthy blood donors and patients with clotting difficulties. Upon receipt, cells were separated from blood plasma by centrifugation and blood plasma frozen (−80° C.) for later experimentation. The thawing procedure consisted of storing the frozen sample in the refrigerator (+5° C.) for 1 hour then in cold water (+10° C.) for 30 minutes. Immediately after thawing, the sample was treated by e-plasma. PT, aPTT, and Thrombin time measurements were obtained.

FE-DBD was experimentally confirmed to significantly hasten blood coagulation. Visually, a drop of blood drawn from a healthy donor and left on a stainless steel surface coagulates on its own in about 15 minutes, while a similar drop treated for 15 seconds by FE-DBD e-plasma coagulates in under 1 minute. FE-DBD treatment of cuts on organs led to similar results where blood is coagulated without any visible or microscopic tissue damage.

A human spleen was treated by FE-DBD for 30 seconds—blood was coagulated and the cut remained at room temperature (even after 5 minutes of FE-DBD treatment) and the wound remained wet, which may, in turn, decrease healing time. Additionally, a significant change in blood plasma protein concentrations was observed after treatment by e-plasma of blood plasma samples from healthy patients, patients with Hemophilia, and blood samples containing various anti-coagulants. For analysis of blood plasma, a set of standard test procedures that are accepted in a hospital setting as determining of the blood coagulation rate, were employed: aPTT (activated Partial Thromboplastin Time), PT (Prothrombin Time), and TT (Thrombin Time). These tests were chosen as they are the most clinically relevant and are used commonly in hospitals to collectively test for the most common clotting pathologies.

The PT measures the clotting time from the activation of factor VII through the formation of fibrin clot. This test measures the integrity of the "Tissue Factor" pathway of coagulation, whereas the aPTT measures the integrity of the "Contact Activation" pathway of coagulation. The TT test is a measure of the rate of conversion of fibrinogen to fibrin when thrombin has been introduced—it measures hemostatically active fibrinogen.

Figure 12:
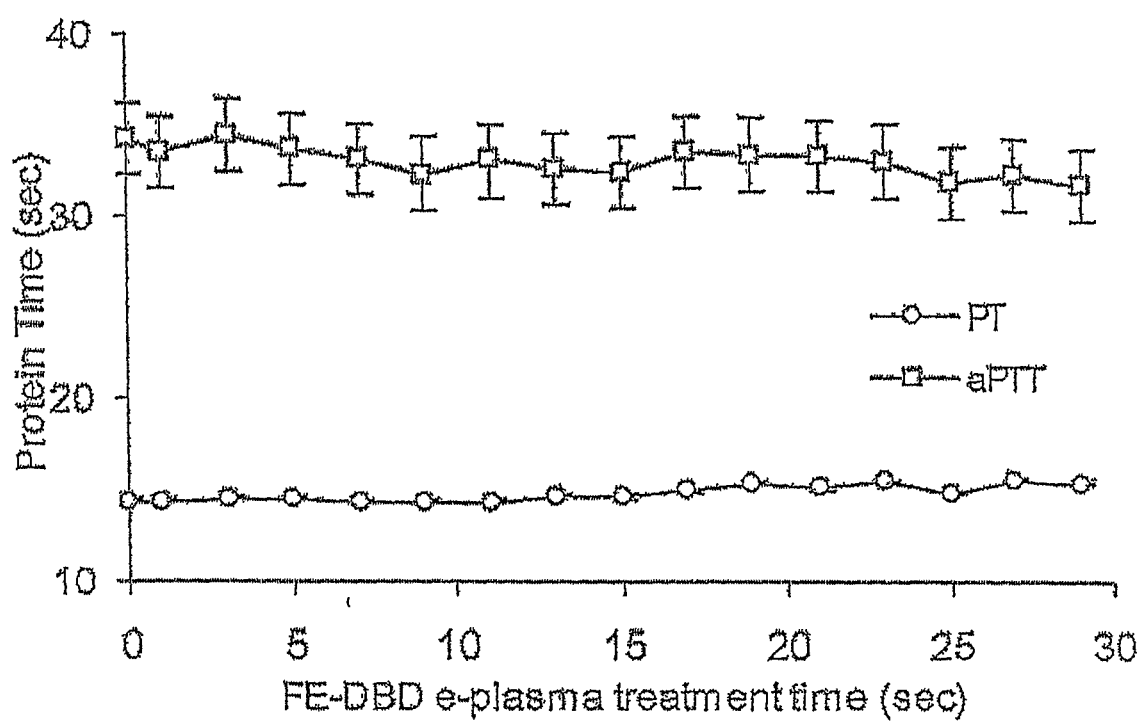
FIG. 12 shows blood plasma Prothrombin Time (hereinafter "PT") and activated Partial Thromboplastin Time (hereinafter "aPTT") behavior prior to film formation: aPTT time (top) and PT time (bottom).
Figure 13:
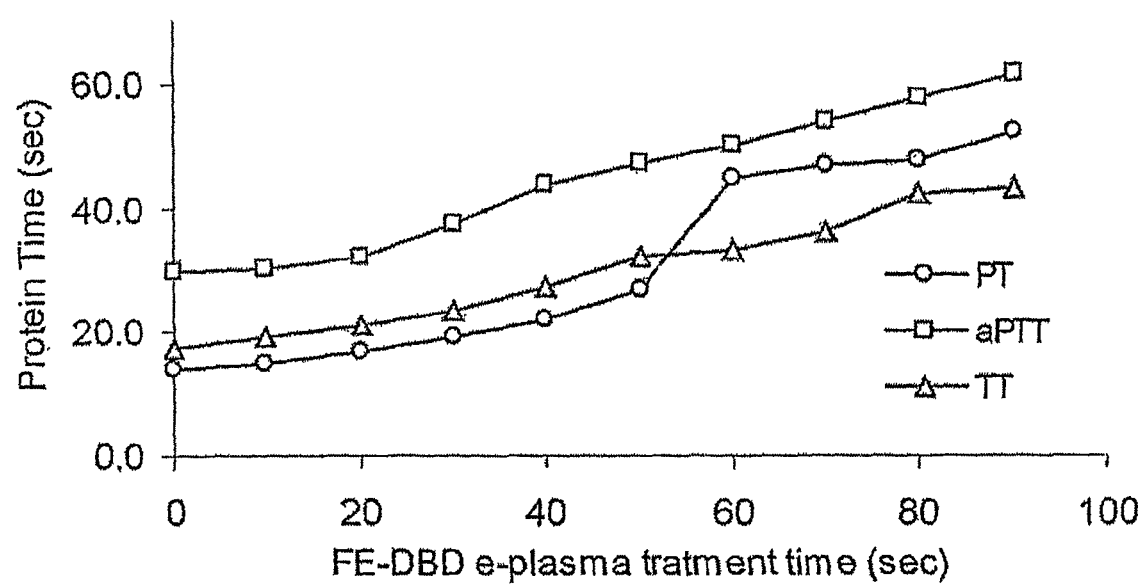
FIG. 13 shows blood plasma behavior at higher FE-DBD doses: PT, aPTT, and Thrombin Time (hereinafter "TT") times.

A significant difference in the coagulation rates were observed even at low doses (a few seconds up to few minutes at ~1 W/cm$^2$) from treatment of blood plasma samples from patients with Hemophilia and for healthy donors. To simplify the analysis of FE-DBD e-plasma and its influence on blood coagulation time, blood plasma was separated from blood cells. These samples were subjected to low doses of FE-DBD e-plasma and analyzed for a few major blood proteins (coagulation factors). Thin transparent film formation on the surface of the sample was observed after about 30 seconds of treatment. PT and aPTT tests of the samples subjected to less than 30 seconds of treatment showed practically no influence of the e-plasma treatment and the blood plasma remained visually intact (FIG. 12). Blood plasma subjected to higher doses of FE-DBD changed its protein and enzyme behavior significantly (FIG. 13).

Figure 14:
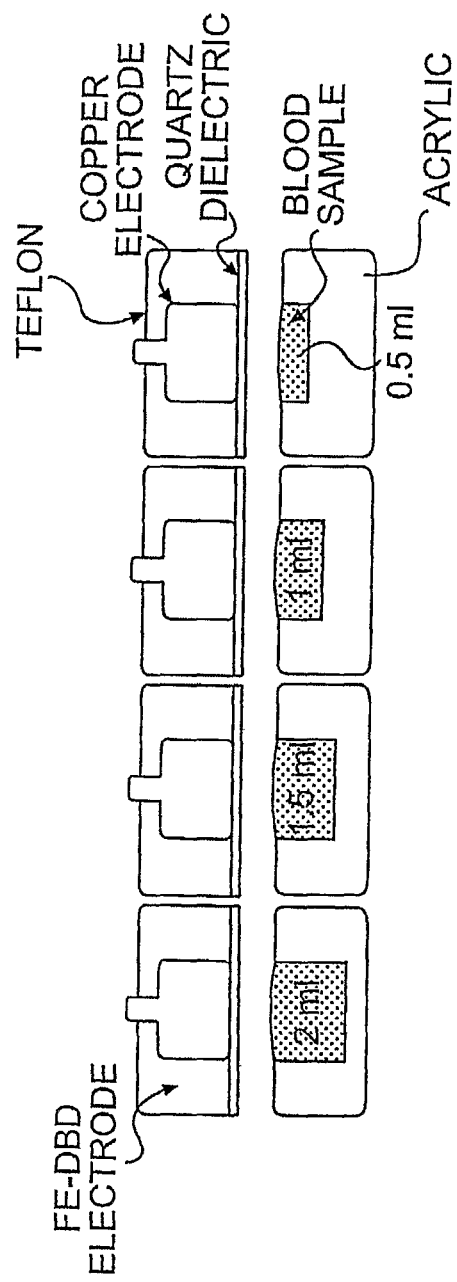
FIG. 14 shows a setup schematic for blood samples of different volumes with the same surface area of FE-DBD treatment.
Figure 15:
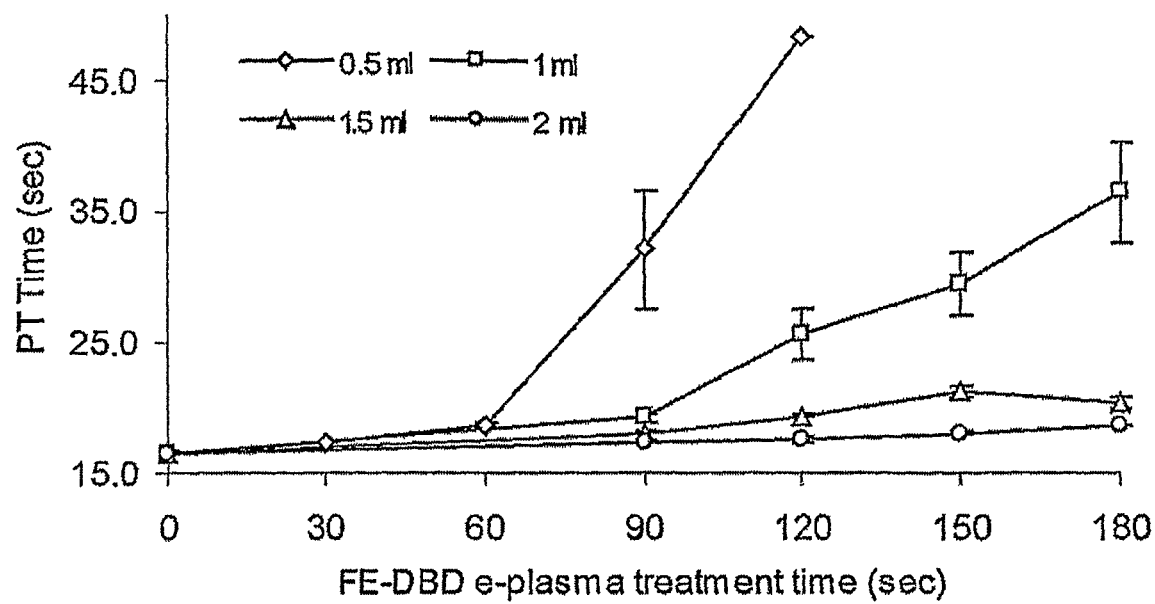
FIG. 15 shows PT times for blood samples of different volumes with the same surface area of FE-DBD treatment.

The observed behavior of blood plasma proteins is somewhat counter-intuitive—one would expect PT time, for example, to go down for blood that coagulates faster. PT time is representative of the time required for normal blood plasma to produce sufficient amount of thrombin, thus finalizing the cascade and forming a blood clot. However, a fixed volume of blood, a portion of which is clotting is depleting itself of proteins required for clotting and thus exhibits longer PT, aPTT, and TT times as is observed (FIG. 13). This was verified by using varying sample volumes at fixed treatment area; in which case it was observed that for different blood volumes with the same surface area of treatment, the same rate of film formation but different rates of protein depletion are obtained (FIG. 14—setup, FIG. 15—results).

Example 5

Tissue Sterilization

Tissue samples were obtained from cadavers, explanted organs, and discarded tissue samples. The samples were swabbed using BD BBL™ CultureSwab™ (Becton, Dickinson and Company, Sparks, Md.) and the swabs were plated and subsequently analyzed. Every tissue sample was swabbed before (control) and after e-plasma treatment to access e-plasma sterilization efficiency.

Bacteria for quantitative analysis of sterilization were obtained by transferring skin flora from a patient with normal skin flora onto a blood agar plate (Trypticase™ Soy Agar with 5% Sheep Blood; Cardinal Health, Dublin, Ohio). After 24 hours at 37° C. in air incubator (Fisher Scientific, Pittsburgh, Pa.) grown colonies were transferred from the agar surface into a sterile container and diluted with purified sterile water. 60 samples were prepared from the original broth and frozen (−80° C.) for later experimentation. The thawing procedure consisted of 30 minutes in cold water (+10° C.). An initial concentration of colony forming units (cfu) was obtained by performing dilution assays of the samples. For experimentation, thawed samples were diluted to the desired concentration and either a 20 µl or 1 ml sample was pipetted onto agar for treatment. 1 ml samples were pipetted onto agar and left to dry for 3 hours in the class I biological safety hood (Fisher Scientific, Pittsburgh, Pa.). 20 µl samples were left to dry for 5 minutes prior to e-plasma treatment and were spread over the agar plate by a sterile swab after treatment (Table 1).

TABLE 1

| Skin flora sterilization | | | |
|---|---|---|---|
| Original Concentration | 5 Seconds of FE-DBD | 10 Seconds of FE-DBD | 15 Seconds of FE-DBD |
| 10$^9$ cfu | 850 ± 183 cfu | 9 ± 3 cfu | 0 ± 4 cfu |
| 10$^8$ cfu | 22 ± 5 cfu | 2 ± 5 cfu | 0 ± 0 cfu |
| 10$^7$ cfu | 2 ± 6 cfu | 0 ± 0 cfu | 0 ± 3 cfu |

Conventional electric discharges (both high and low pressure and temperature) are well-known for their ability to sterilize various surfaces. The advantage of the present FE-DBD system is its ability to sterilize living animal or human tissue without significant damage to the treated tissue. These tests confirmed that there was no gross (visible) or histological (microscopic) damage to the treated skin and organ samples after as much as 5 minutes of treatment while complete hospital-grade sterilization is achieved in less than 6 seconds of e-plasma treatment.

Growth of normal skin flora (mixture of *Streptococcus, Staphylococcus*, and *Yeast*) was noted for cultures from swabs taken on control samples, no growth was noted on cultures from swabs taken on samples treated by e-plasma for 2 to 6 seconds, depending on the level of initial contamination of the skin. Skin samples treated by e-plasma show no visible damage and histological analysis shows no microscopic damage.

Figure 16:
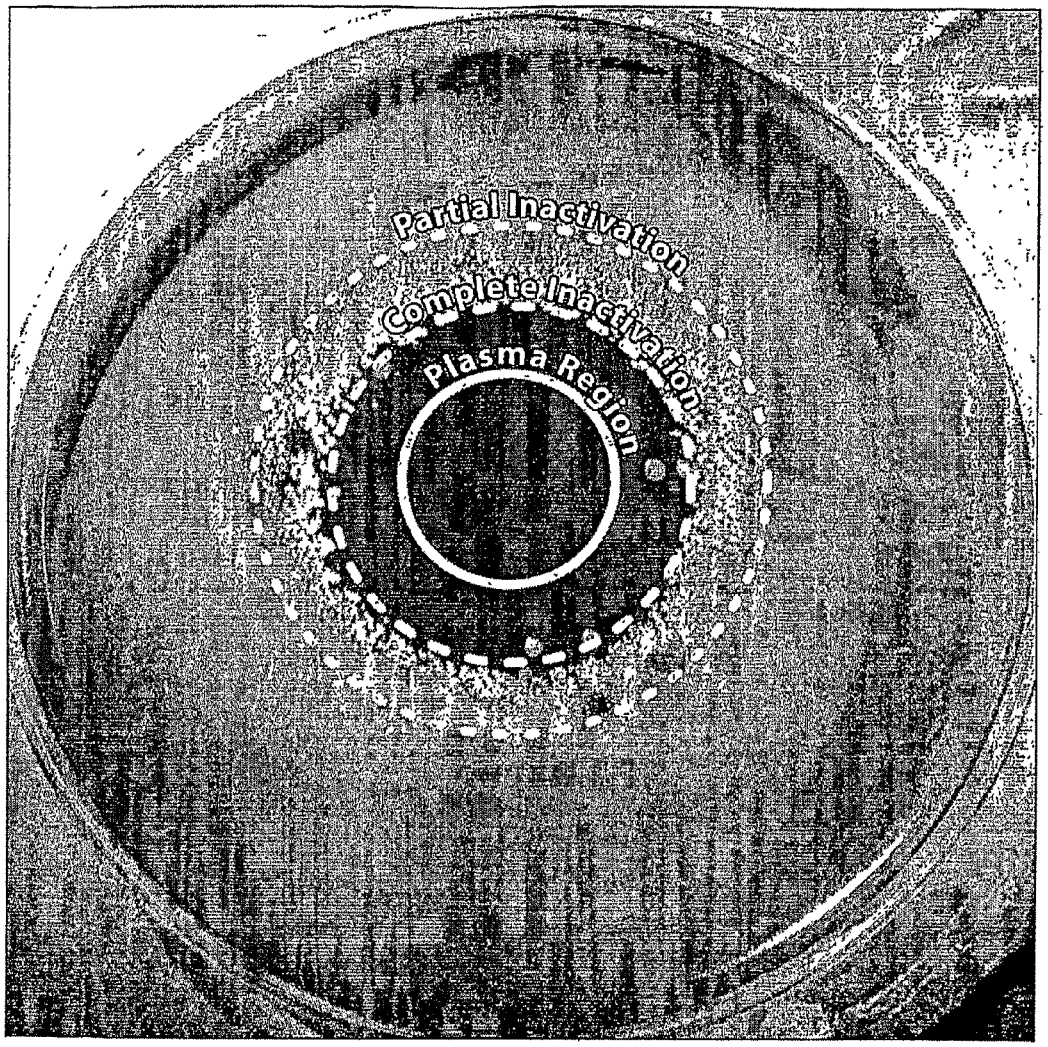
FIG. 16 shows a Petri dish with blood agar, seeded by ~1.3·$10^7$ colony forming units (hereinafter "cfu") per $cm^2$ ($10^9$ cfu/ml) of skin flora and then treated by FE-DBD plasma for 10 seconds. While the plasma region diameter is roughly 25 mm, the "inner" circle of inactivated bacteria and fungi diameter is ~35 mm and the "outer" circle where the bacteria is partially inactivated (colonies are visible) is ~54 mm.
Figure 17:
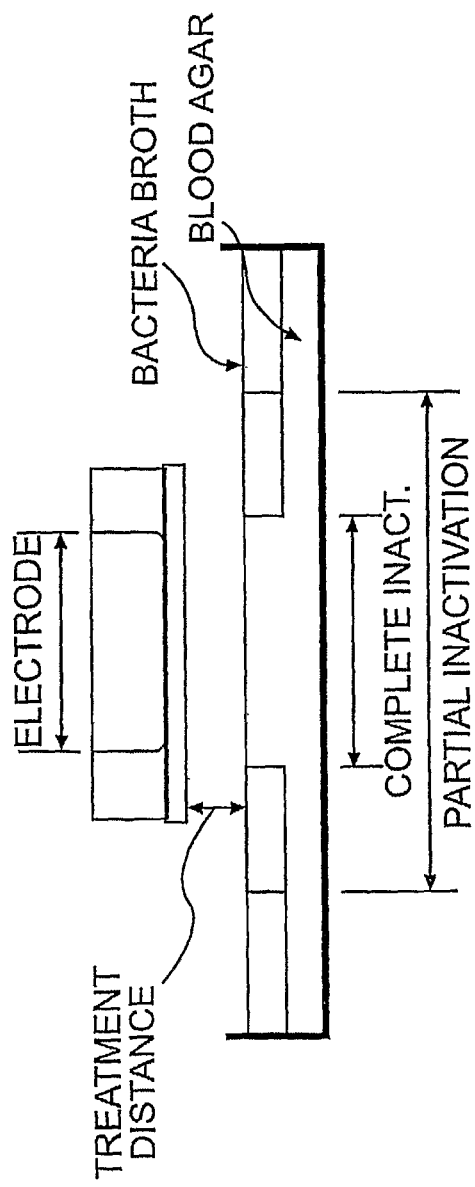
FIG. 17 is a schematic illustration of FE-DBD treatment of agar dishes with bacterial broth.
Figure 18:
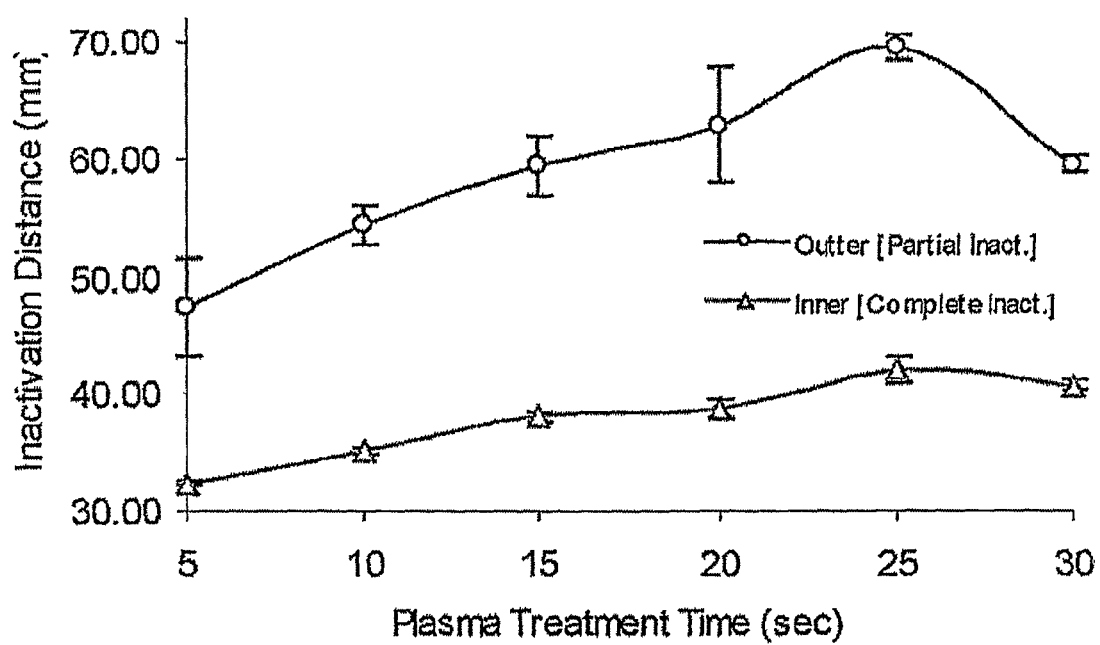
FIG. 18 shows the dependence of the inner circle diameter (bottom) and outer circle diameter (top) of skin flora inactivation on FE-DBD treatment time.

Following the qualitative test of human skin tissue, the effects of e-plasma on bacterial cultures was investigated to quantify the extent of sterilization and determine possible factors responsible. A large quantity of bacteria obtained from a swab of cadaver tissue was cultured on blood agar. The concentration of $10^9$ colony forming units (cfu) per milliliter of liquid was chosen as it is roughly 10,000 times greater than that on normal skin. The prepared culture plates were treated by FE-DBD and the plates were then incubated for 24 hours. No growth was observed on the areas treated by FE-DBD for a few seconds (FIG. 16) and the extent of e-plasma sterilization was quantified (Table 1) based on the treatment dose. With increased dose it was possible to sterilize an area quite far from the treatment electrode (FIG. 17—schematic illustration and FIG. 18—results). Of note is no visible damage to the agar even at higher doses—bacteria grows on the treated agar normally, if re-inoculated. Even when a fan was employed to flow air through e-plasma at high rate the "complete inactivation" shifts only slightly and remains practically independent of the flow rate employed. These results suggest that direct treatment by plasma is more potent in bacterial activation than indirect treatment (by a jet, for example).

Example 6

*Leishmania*

*Leishmania* is a skin disease induced by a bite of an infected sandfly. *Leishmania* develops in several stages:
- (a) a sandfly injects promastigotes into the body when feeding on the body,
- (b) promastigotes are phagocytized by macrophages,
- (c) promastigotes are transformed into amastigotes inside macrophages,
- (d) amastigotes multiply and burst out of the macrophage, and
- (e) these amastigotes are phagocytized by macrophages thereby completing the process, repeating steps (d) and (e) until no macrophages remain or the host system is dead.

Figure 19:
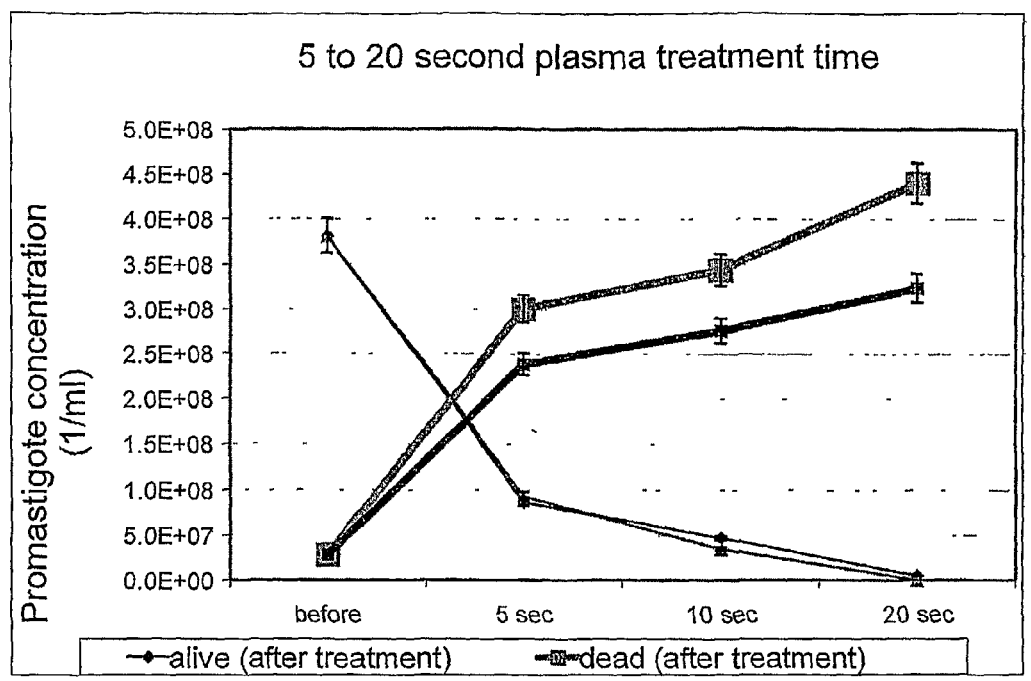
FIG. 19 shows *Leishmania* promastigote parasite inactivation using different lengths of non-thermal plasma treatment.
Figure 20:
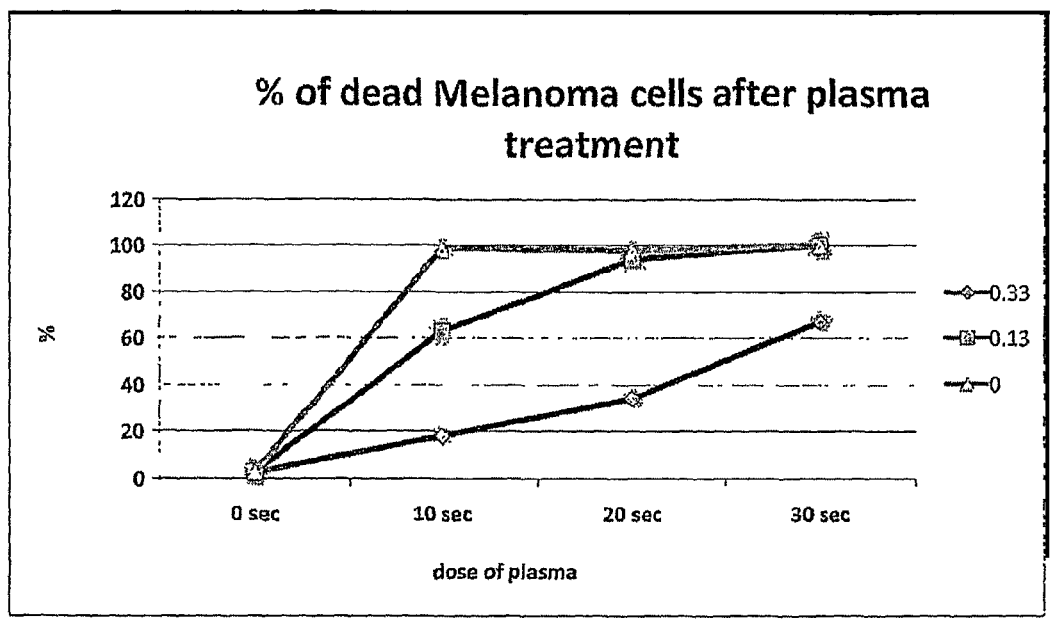
FIG. 20 shows the effectiveness of the non-thermal plasma treatments at different depths of penetration given in millimeters.

*L. Major* promastigotes and macrophages were obtained and treated separately with non-thermal plasma discharges. 30-50% of macrophages were inactivated after 2 minutes of treatment with non-thermal plasma. 100% of promastigotes were inactivated after 20 seconds of treatment with non-thermal plasma (FIG. 19). As a result, the non-thermal plasma treatment can be employed to selectively inactivate certain prokaryotic cells, such as the promastigotes, without causing damage to the surrounding tissue. Treatment of *Leishmania* at different treatment depths was also tested. The results of this testing are shown in FIG. 20 for treatment depths given in millimeters.

Example 7

Apoptosis of Melanoma Cells

Figure 21:
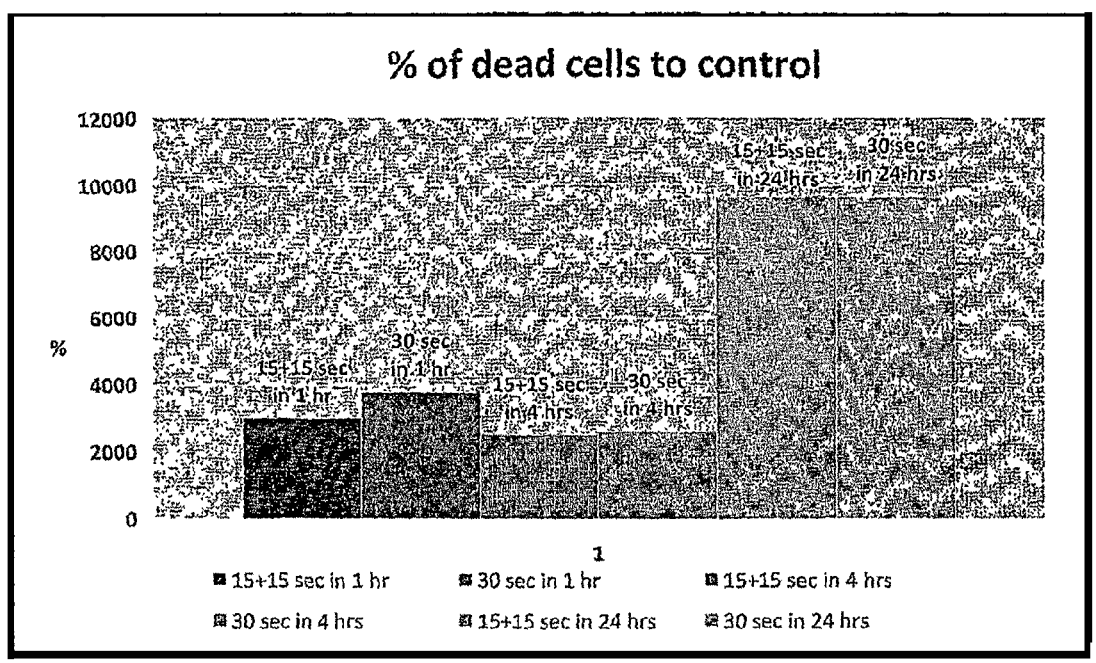
FIG. 21 shows the effectiveness of the non-thermal plasma treatments at inducing apoptosis of human melanoma cancer cells.

Non-thermal plasma treatments, as described above, were also employed to treat melanoma cells. FIG. 21 shows that the non-thermal plasma treatment was extremely effective at inducing apoptosis of melanoma cells, relative to the control.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A method of non-thermal treatment of living tissue comprising the step of generating a non-thermal gas discharge plasma proximate to a surface of the living tissue by causing sufficient electrical current to pass through the tissue to provide said gas discharge plasma, by using a device comprising a high voltage electrode and an insulative or semiconductive barrier, said non-thermal plasma being generated by a high frequency oscillation of high voltage of from about 5 to about 20,000 kHz using a voltage of about 2 to about 50 kV, said device configured for placement proximate to said living tissue with the barrier positioned between the electrode and living tissue, said device capable of passing a current from the electrode to and through the tissue at a current density sufficient to generate a gas discharge plasma proximate to the tissue, said current being limited by the presence of the barrier between the tissue and the electrode.

2. A method as claimed in claim 1, wherein a specific electric plasma discharge power of said gas discharge plasma is greater than 0.01 Watt/cm$^2$, averaged over one square millimeter of a treatment area.

3. A method as claimed in claim 2, wherein the specific electric plasma discharge power of said gas discharge plasma is greater than 0.1 Watt/cm$^2$, averaged over one square millimeter of a treatment area.

4. A method as claimed in claim 1, wherein the gas discharge is a high-voltage discharge, and a value of the electric field near the surface of the living tissue exceeds 200 V/mm in the moments of maximal current.

5. A method as claimed in claim 1, wherein the gas discharge is a high-voltage discharge, and a value of the electric field near the surface of the living tissue exceeds 500 V/mm in the moments of maximal current.

6. A method as claimed in claim 1, wherein a gas in the gas discharge plasma is air that naturally exists near the surface of the living tissue.

7. A method as claimed in claim 1, wherein a gas in the gas discharge plasma is a pure gas.

8. A method as claimed in claim 1, wherein a gas of the gas discharge plasma comprises additives of pure gases.

9. A method as claimed in claim 8, wherein said additives of pure gases comprise hydrogen peroxide, an alcohol vapor, methane, or ethane.

10. A method as claimed in claim 1, wherein a gas in the gas discharge plasma is caused to flow relative to a treatment area.

11. A method as claimed in claim 1, wherein said treatment of living tissue kills a bacteria, virus, micro-organism, or destroys a protein that may exist on or within said tissue.

12. A method as claimed in claim 1, wherein said treatment of living tissue treats a disease or a wound.

13. A method as claimed in claim 1, wherein said treatment of living tissue provides a cosmetic improvement.

14. A method as claimed in claim 1, wherein said treatment of living tissue coagulates blood.

15. A method as claimed in claim 1, wherein said treatment of living tissue destroys certain cells within a surface layer of the said tissue.

16. A method as claimed in claim 1, wherein said treatment of living tissue triggers apoptosis of certain tissue cells.

17. A method as claimed in claim 1, wherein said treatment of living tissue improves a mechanical connection between different parts of the tissue.

18. A method as claimed in claim 1, wherein said non-thermal plasma is generated by a high frequency oscillation of high voltage of from about 10 to about 30 kHz.

19. A method as claimed in claim 1, wherein said non-thermal plasma is generated using a voltage of about 10 to about 30 kV.

* * * * *

UNITED STATES PATENT AND TRADEMARK OFFICE
CERTIFICATE OF CORRECTION

PATENT NO. : 8,521,274 B2
APPLICATION NO. : 11/911479
DATED : August 27, 2013
INVENTOR(S) : Gutsol et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1458 days.

Signed and Sealed this
Fifteenth Day of September, 2015

Michelle K. Lee
*Director of the United States Patent and Trademark Office*